(12) United States Patent
Thompson et al.

(10) Patent No.: US 8,580,985 B2
(45) Date of Patent: Nov. 12, 2013

(54) PROCESSES FOR PREPARING ESTOLIDE BASE OILS AND OLIGOMERIC COMPOUNDS THAT INCLUDE CROSS METATHESIS

(71) Applicant: Biosynthetic Technologies, LLC, Irvine, CA (US)

(72) Inventors: Travis Thompson, Anaheim, CA (US); Kelly Parson, Irvine, CA (US); Jakob Bredsguard, Irvine, CA (US); Jeremy Forest, Irvine, CA (US)

(73) Assignee: Biosynthetic Technologies, LLC, Irvine, CA (US)

( * ) Notice: Subject to any disclaimer, the term of this patent is extended or adjusted under 35 U.S.C. 154(b) by 0 days.

(21) Appl. No.: 13/707,480

(22) Filed: Dec. 6, 2012

(65) Prior Publication Data

US 2013/0158277 A1    Jun. 20, 2013

Related U.S. Application Data

(60) Provisional application No. 61/577,598, filed on Dec. 19, 2011, provisional application No. 61/610,376, filed on Mar. 13, 2012.

(51) Int. Cl.
*C07C 59/235* (2006.01)
*C07C 69/66* (2006.01)
*C07C 69/34* (2006.01)
*C10M 105/36* (2006.01)

(52) U.S. Cl.
USPC ........... 554/122; 560/185; 508/465; 508/496; 508/506; 554/163

(58) Field of Classification Search
None
See application file for complete search history.

(56) References Cited

U.S. PATENT DOCUMENTS

| | | | |
|---|---|---|---|
| 5,011,629 A | 4/1991 | Bilbo | |
| 5,021,311 A * | 6/1991 | Kato et al. | 430/96 |
| 5,380,894 A | 1/1995 | Burg et al. | |
| 5,427,704 A * | 6/1995 | Lawate | 508/491 |
| 5,451,332 A | 9/1995 | Lawate | |
| 6,018,063 A | 1/2000 | Isbell et al. | |
| 6,316,649 B1 | 11/2001 | Cermak et al. | |
| 7,119,216 B2 | 10/2006 | Newman et al. | |
| 7,960,599 B2 | 6/2011 | Millis et al. | |
| 8,115,021 B2 | 2/2012 | Tupy et al. | |
| 8,258,326 B1 | 9/2012 | Forest et al. | |
| 2010/0120643 A1 | 5/2010 | Brown et al. | |
| 2010/0145086 A1 | 6/2010 | Schrodi et al. | |
| 2012/0172609 A1 | 7/2012 | Bredsguard et al. | |

FOREIGN PATENT DOCUMENTS

| | | | |
|---|---|---|---|
| EP | 0 665 284 A2 | 8/1995 | |
| FR | 2906530 A1 | 4/2008 | |
| JP | 05150560 A * | 6/1993 | ............... G03G 9/13 |
| JP | 2002196543 * | 7/2002 | ............... C08F 2/08 |
| JP | 2004051789 * | 2/2004 | ............... B41J 2/01 |
| WO | WO-01/53247 A1 | 7/2001 | |
| WO | WO-03/011455 A1 | 2/2003 | |
| WO | WO-2012/030398 A1 | 3/2012 | |
| WO | WO-2012/061101 A1 | 5/2012 | |

OTHER PUBLICATIONS

Troast, D.M., et al., Studies Toward the synthesis of (−)-Zampanolide: preparation of n-acyl hemiaminal model systems, 2002, Organic letters, vol. 4, No. 6, pp. 991-994.*
Dobbs, A. P., et al., First total synthesis of the irciniasulfonic acids, 2005, Synlett, No. 4, pp. 0652-0654.*
Dorwald, F.A., Side reactions in organic synthesis, 2005, Wiley:VCH, Weinheim pp. 1-15 (20 pages with cover).*
Kato, E., Liquid Developer for electrostatic photograph, 2002, JP20022196543(A), English abstract, 1 page.*
Kato, E., Oily ind for electrostatic inkjet platemaking, 2002, JP 2004051789(A), English abstract, 1 page.*
Co-Pending U.S. Appl. No. 13/787,556, filed Mar. 6, 2013.
Cann et al., "Polymerization of Undecylenic Acid in the Presence of Boron Fluoride," *J. Am. Chem. Soc.*, 66(5): 839-840 (1944).
Meier et al., "Plant Oil Renewable Resources as Green Alternatives in Polymer Science," *Chem. Soc. Rev.*, 36: 1788-1802 (2007).

(Continued)

*Primary Examiner* — Yate K Cutliff
(74) *Attorney, Agent, or Firm* — Jeremy Forest

(57) ABSTRACT

Provided herein are estolide base oils and oligomeric compounds prepared from processes that include cross metathesis. Exemplary processes include the preparation of terminally-unsaturated fatty acids by cross metathesis, and the subsequent oligomerization of terminally-unsaturated fatty acids to provide estolide compounds, such as the process set forth below:

19 Claims, No Drawings

(56) References Cited

OTHER PUBLICATIONS

Mol et al., "Catalytic Metathesis of Unsaturated Fatty Acid Esters and Oils," *Topics in Catalysis*, 27, Nos. 1-4: 97-104 (2004).
Ross et al., "The Polymerization of Undecylenic Acid," *J. Am. Chem. Soc.*, 67(8): 1275-1278 (1945).
Skupinska et al., "Oligomerization of a-Olefins to Higher Oligomers," *Chem. Rev.*, 91: 613-648 (1991).
International Search Report and Written Opinion mailed Nov. 23, 2011 in International Application No. PCT/US2011/001540.
Article 19 Amendments and Letter Accompanying Replacement Sheets for counterpart application PCT/US2011/001540, filed Jan. 28, 2012.
Reply to Written Opinion for counterpart application PCT/US2011/001540, filed Jun. 28, 2012.
Written Opinion of the International Preliminary Examining Authority for counterpart application PCT/US2011/001540, filed Jun. 28, 2012.
International Preliminary Report on Patentability for counterpart application PCT/US2011/001540, mailed Nov. 15, 2012.
Erhan et al., "Estolides from Meadowfoam Oil Fatty Acids and Other Monounsaturated Fatty Acids," *JAOCS*, 70:5, 461-465 (May 1993).
Isbell et al., "Acid-Catalyzed Condensation of Oleic Acid into Estolides and Polyestolides," *JAOCS*, 71(2): 169-74 (1994).
Ishihara et al., "Direct Condensation of Carboxylic Acids with Alcohols Catalyzed by Hafnium(IV) Salts," *Science*, 290: 1140-42 (2000).
Kulkarni et al., "Kinetics of the Catalytic Esterification of Castor Oil with Lauric Acid Using n-Butyl Benzene as a Water Entrainer," *JAOCS*, 80:10, 1033-1038 (2003).
Kwie et al., "Bismuth (III) Triflate: A Safe and Easily Handled Precursor for Triflic Acid: Application to the Esterification Reaction," *Syn. Comm.*, 40: 1082-1087 (2010).
Lotero et al., "Synthesis of Biodiesel via Acid Catalysis," *Ind. Eng. Chem.*, 44: 5353-5363 (2005).
Co-Pending U.S. Appl. No. 13/199,551, filed Aug. 31, 2011.
Co-Pending U.S. Appl. No. 13/875,172, filed May 1, 2013.
International Search Report and Written Opinion mailed Apr. 24, 2013 in counterpart International Application No. PCT/US2012/068293.
Abstract of JP 5-150560, published Jun. 18, 1993.
Ahmad et al., "Oleochemicals from Isoricinoleic Acid (*Wrightia tinctoria* Seed Oil)", *Ind. Eng. Chem. Res.*, 47: 2091-2095 (2008).
Cermak et al., "Synthesis and Physical Properties of New Estolide Esters", *Industrial Crops and Products*, 46: 386-391 (2013).
Garcia-Zapateiro et al., "Viscous, thermal and tribological characterization of oleic and ricinoleic acids-derived estolides and their blends with vegetable oils", *Journal of Indus. And Engin. Chem.*, 19: 1289-1298 (2013).
International Search Report and Written Opinion for international application PCT/US2013/029426, mailed Jun. 6, 2013.

\* cited by examiner

PROCESSES FOR PREPARING ESTOLIDE BASE OILS AND OLIGOMERIC COMPOUNDS THAT INCLUDE CROSS METATHESIS

CROSS-REFERENCE TO RELATED APPLICATIONS

This application claims the benefit under 35 U.S.C. §119(e) of U.S. Provisional Patent Application No. 61/577,598, filed Dec. 19, 2011, and U.S. Provisional Patent Application No. 61/610,376, filed Mar. 13, 2012, both of which are incorporated herein by reference in their entireties for all purposes.

FIELD

The present disclosure relates to estolide base oils, oil stocks, lubricants, and oligomeric compounds, and methods of making the same. Exemplary processes include the use of cross metathesis.

BACKGROUND

Lubricant compositions typically comprise a base oil, such as a hydrocarbon base oil, and one or more additives. Estolides present a potential source of biobased, biodegradable oils that may be useful as lubricants and base stocks. In addition, certain oligomeric compounds, such as estolides prepared from fatty acids having terminal sites of unsaturation, may provide biodegradable high-viscosity oils and other polymeric-type compounds.

SUMMARY

Described herein are estolide compounds and compositions, oligomeric compounds, and methods of making the same. In certain embodiments, such compounds and compositions may be useful as base oils and lubricants. Also described herein are oligomeric/polymeric compounds and compositions that may be useful as high-viscosity oils or film-like materials and coatings.

In certain embodiments are described at least one compound of Formula I:

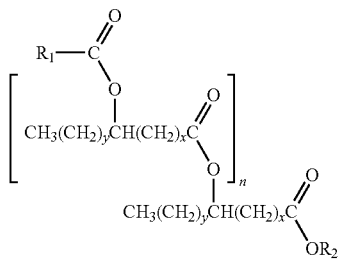

Formula I wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer equal to or greater than 0;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted, and wherein, for at least one fatty acid chain residue, x is an integer selected from 7 and 8 and y is an integer selected from 0, 1, 2, 3, 4, 5, and 6.

In certain embodiments are described at least one compound of Formula II:

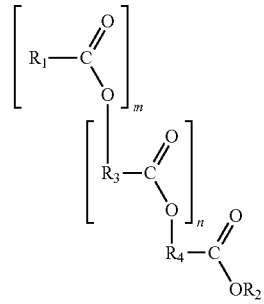

Formula II wherein m is an integer equal to or greater than 1;

n is an integer equal to or greater than 0;

$R_1$ is an optionally substituted, branched or unbranched alkyl that is saturated or unsaturated;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$, $R_3$, and $R_4$ comprises an unbranched undecanyl that is saturated or unsaturated.

In certain embodiments are described a process of producing an estolide base oil comprising:

providing at least one fatty acid substrate having at least one fatty acid residue with at least one internal site of unsaturation;

providing at least one alpha olefin;

contacting the at least one fatty acid substrate with the at least one alpha olefin in the presence of a metathesis catalyst to provide an olefin product and a metathesized fatty acid product;

optionally converting the metathesized fatty acid product into at least one first fatty acid product;

optionally providing at least one second fatty acid reactant;

providing an oligomerization catalyst; and oligomerizing the metathesized fatty acid product and/or first fatty acid product, optionally with the at least one second fatty acid reactant, in the presence of the oligomerization catalyst to produce an estolide base oil.

In certain embodiments the estolides comprise at least one compound of Formula III:

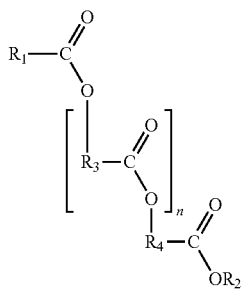

Formula III wherein
n is an integer equal to or greater than 0;
$R_1$ is an optionally substituted, branched or unbranched alkyl that is saturated or unsaturated;
$R_2$ is selected from hydrogen and optionally substituted alkyl that is saturated or unsaturated, and branched or unbranched; and
$R_3$ and $R_4$, independently for each occurrence, are selected from

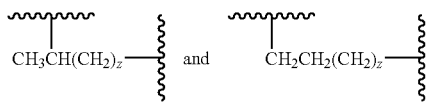

wherein $R_3$ and $R_4$ are independently optionally substituted and z is, independently for each occurrence, an integer selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40.

In certain embodiments are described a process of producing an estolide base oil, comprising:
providing at least one estolide compound having at least one fatty acid chain residue with at least one internal site of unsaturation;
providing at least one olefin reactant; and
contacting the at least one estolide compound with the at least olefin reactant in the presence of a metathesis catalyst to provide an olefin product and an estolide base oil, wherein said estolide base oil comprises at least one fatty acid chain residue with at least one terminal site of unsaturation or at least one internal site of unsaturation.

A process of producing an oligomeric compound is also described. In certain embodiments, the process comprises:
providing at least one first fatty acid reactant and at least one second fatty acid reactant, wherein the at least one second fatty acid reactant has at least one terminal site of unsaturation; and
reacting the at least one first fatty acid reactant with the at least one second fatty acid reactant to provide a compound, wherein a covalent bond is formed between an oxygen of a carboxylic group of the at least one first fatty acid reactant and a carbon of the at least one terminal site of unsaturation of the at least one second fatty acid reactant.

In certain embodiments, the estolides comprise at least one compound of Formula V:

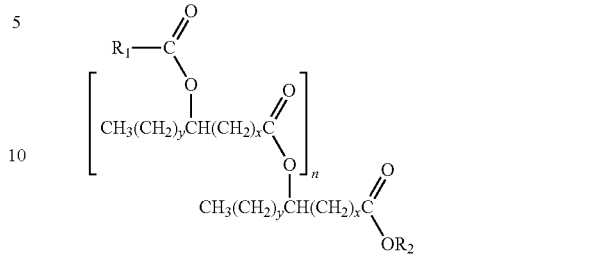

Formula V wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is an integer equal to or greater than 0;
$R_1$ is an optionally substituted, branched or unbranched alkyl having at least one terminal site of unsaturation; and
$R_2$ is selected from hydrogen and an optionally substituted alkyl that is saturated or unsaturated, and branched or unbranched,
wherein each fatty acid chain residue of said at least one compound is independently optionally substituted.

DETAILED DESCRIPTION

The use of lubricants and lubricant-containing compositions may result in the dispersion of such fluids, compounds, and/or compositions in the environment. Petroleum base oils used in common lubricant compositions, as well as additives, are typically non-biodegradable and can be toxic. The present disclosure provides for the preparation and use of compositions comprising partially or fully biodegradable base oils, including base oils comprising one or more estolides.

In certain embodiments, the compositions comprising one or more estolides are partially or fully biodegradable and thereby pose diminished risk to the environment. In certain embodiments, the compositions meet guidelines set for by the Organization for Economic Cooperation and Development (OECD) for degradation and accumulation testing. The OECD has indicated that several tests may be used to determine the "ready biodegradability" of organic chemicals. Aerobic ready biodegradability by OECD 301D measures the mineralization of the test sample to $CO_2$ in closed aerobic microcosms that simulate an aerobic aquatic environment, with microorganisms seeded from a waste-water treatment plant. OECD 301D is considered representative of most aerobic environments that are likely to receive waste materials. Aerobic "ultimate biodegradability" can be determined by OECD 302D. Under OECD 302D, microorganisms are pre-acclimated to biodegradation of the test material during a pre-incubation period, then incubated in sealed vessels with relatively high concentrations of microorganisms and enriched mineral salts medium. OECD 302D ultimately determines whether the test materials are completely biodegradable, albeit under less stringent conditions than "ready biodegradability" assays.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH$_2$ is attached through the carbon atom.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is C$_{7-30}$ arylalkyl, e.g., the alkanyl, alkenyl, or alkynyl moiety of the arylalkyl group is C$_{1-10}$ and the aryl moiety is C$_{6-20}$, and in certain embodiments, an arylalkyl group is C$_{7-20}$ arylalkyl, e.g., the alkanyl, alkenyl, or alkynyl moiety of the arylalkyl group is C$_{1-8}$ and the aryl moiety is C$_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

The term "catalyst" refers to single chemical species; physical combinations of chemical species, such as mixtures, alloys, and the like; and combinations of one or more catalyst within the same region or location of a reactor or reaction vessel. Examples of catalyst include, e.g., Lewis acids, Bronsted acids, and Bismuth catalysts, wherein Lewis acids, Bronsted acids, and Bismuth catalysts may be single chemical species; physical combinations of chemical species, such as mixtures, alloys, and the like; and combinations of one or more catalyst within the same region or location of a reactor or reaction vessel.

"Compounds" refers to compounds encompassed by structural Formula I, II, III, IV, and V herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I, II, III, IV, and V include, but are not limited to, optical isomers of compounds of Formula I, II, III, IV, and V, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I, II, III, IV, and V cover all asymmetric variants of the compounds described herein, including isomers, racemates, enantiomers, diastereomers, and other mixtures thereof. In addition, compounds of Formula I, II, III, IV, and V include Z- and E-forms (e.g., cis- and trans-forms) of compounds with double bonds. The compounds of Formula I, II, III, IV, and V may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkenyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Solid-supported acid" refers to an acidic compound or material that is supported by or attached to another compound or material comprising a solid or semi-solid structure. Such materials include smooth supports (e.g., metal, glass, plastic, silicon, carbon (e.g., diamond, graphite, nanotubes, fullerenes (e.g., C-60)) and ceramic surfaces) as well as textured and porous materials such as clays and clay-like materials. Such materials also include, but are not limited to, gels, rubbers, polymers, and other non-rigid materials. Solid supports need not be composed of a single material. By way of example but not by way of limitation, a solid support may comprise a surface material (e.g. a layer or coating) and a different supporting material (e.g., coated glass, coated metals and plastics, etc.) In some embodiments, solid-supported acids comprise two or more different materials, e.g., in layers. Surface layers and coatings may be of any configuration and may partially or completely cover a supporting material. It is contemplated that solid supports may comprise any combination of layers, coatings, or other configurations of multiple materials. In some embodiments, a single material provides essentially all of the surface to which other material can be attached, while in other embodiments, multiple materials of the solid support are exposed for attachment of another material. Solid supports need not be flat. Supports include any type of shape including spherical shapes (e.g., beads). Acidic moieties attached to solid support may be attached to any portion of the solid support (e.g., may be attached to an interior portion of a porous solid support material). Exemplary solid-supported acids include, but are not limited to, cation exchange resins (e.g., Amberlyst®, Dowex®); acid-activated clays (e.g., montmorillonites); polymer-supported sulfonic acids (e.g., Nafion®); and silica-support catalysts (e.g., SPA-2).

"Substituted" refers to a group in which one or more hydrogen atoms are independently replaced with the same or different substituent(s). Examples of substituents include, but are not limited to, $-R^{64}$, $-R^{60}$, $-O^-$, $-OH$, $=O$, $-OR^{60}$, $-SR^{60}$, $-S^-$, $=S$, $-NR^{60}R^{61}$, $=NR^{60}$, $-CN$, $-CF_3$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$, $-C(NR^{62})NR^{60}R^{61}$, $-S(O)_2$, $-NR^{60}R^{61}$, $NR^{63}S(O)_2R^{60}$, $-NR^{63}C(O)R^{60}$, and $-S(O)R^{60}$;

wherein each $-R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, —O-haloalkyl, -alkyl-NH$_2$, alkoxy, cycloalkyl, cycloalkylalkyl, heterocycloalkyl, heterocycloalkylalkyl, aryl, heteroaryl, arylalkyl, heteroarylalkyl, —O$^-$, —OH, =O, —O-alkyl, —O—aryl, —O-heteroarylalkyl, —O-cycloalkyl, —O-heterocycloalkyl, —SH, —S$^-$, —S, —S-alkyl, —S-aryl, —S-heteroarylalkyl, —S-cycloalkyl, —S-heterocycloalkyl, —NH$_2$, =NH, —CN, —CF$_3$, —OCN, —SCN, —NO, —NO$_2$, =N$_2$, —N$_3$, —(O)$_2$O, —S(O)$_2$, —S(O)$_2$OH, —OS(O$_2$)O, —SO$_2$(alkyl), —SO$_2$(phenyl), —SO$_2$(haloalkyl), —SO$_2$NH$_2$, —SO$_2$NH(alkyl), —SO$_2$NH(phenyl), —P(O)(O$^-$)$_2$, —P(O)(O-alkyl)(O$^-$), —OP(O)(O-alkyl)(O-alkyl), —CO$_2$H, —C(O)O(alkyl), —CON(alkyl)(alkyl), —CONH(alkyl), —CONH$_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

The term "fatty acid" refers to any natural or synthetic carboxylic acid comprising an alkyl chain that may be saturated, monounsaturated, or polyunsaturated, and may have straight or branched chains. The fatty acid may also be substituted. "Fatty acid," as used herein, includes short chain alkyl carboxylic acids including, for example, acetic acid, propionic acid, etc.

The terms "fatty acid reactant", "fatty acid product" and "fatty acid substrate" refer to any compound or composition comprising at least one fatty acid residue. For example, in certain embodiments, the fatty acid reactant or product may comprise a saturated or unsaturated fatty acid, fatty acid alkyl ester (e.g., methyl stearate, 9-dodecenoic acid methyl ester), fatty acid glyceride (e.g., triglyceride, monoglyceride), or fatty acid oligomer. In certain embodiments, a fatty acid oligomer may comprise a first fatty acid that has previously undergone oligomerization with one or more second fatty acids to form an estolide, such as an estolide having a low EN (e.g., dimer). In certain embodiments, that fatty acid reactant or product is capable of undergoing oligomerization with another fatty acid or fatty acid reactant. For example, the fatty acid reactant or product may comprise a fatty acid residue having at least one site of unsaturation and, thus, may be capable of undergoing oligomerization with another fatty acid reactant or product (e.g., saturated or unsaturated fatty acid). It is understood that a "first" fatty acid reactant can comprise the same structure as a first fatty acid "product" or a "second" fatty acid reactant. For example, in certain embodiments, a reaction mixture may only comprise oleic acid, wherein the first fatty acid reactant and second fatty acid reactant are both oleic acid.

The term "acid-activated clay" refers to clays that are derived from the naturally occurring ore bentonite or the mineral montmorillonite and includes materials prepared by calcination, washing or leaching with mineral acid, ion exchange or any combination thereof, including materials which are often called montmorillonites, acid-activated montmorillonites and activated montmorillonites. In certain embodiments, these clays may contain Bronsted as well as Lewis acid active sites with many of the acidic sites located within the clay lattice. Such clays include, but are not limited to the materials denoted as montmorillonite K10, montmorillonite clay, clayzic, clayfen, the Engelhardt series of catalysts related to and including X-9107, X9105, Girdler KSF, Tonsil and K-catalysts derived from montmorillonite, including but not limited to K5, K10, K20 and K30, KSF, KSF/O, and KP10. Other acid-activated clays may include X-9105 and X-9107 acid washed clay catalysts marketed by Engelhard.

The term "zeolite" refers to mesoporous aluminosilicates of the group IA or group IIA elements and are related to montmorillonite clays that are or have been acid activated. Zeolites may comprise what is considered an "infinitely" extending framework of AlO$_4$ and SiO$_4$ tetrahedra linked to each other by the sharing of oxygens. The framework structure may contain channels or interconnecting voids that are occupied by cations and water molecules. Acidic character may be imparted or enhanced by ion exchange of the cations, such as with ammonium ions and subsequent thermal deamination or calcination. The acidic sites may primarily be located within the lattice pores and channels. In certain instances, zeolites include, but are not limited to, the beta-type zeolites as typified by CP814E manufactured by Zeolyst International, the mordenite form of zeolites as typified by CBV21A manufactured by Zeolyst International, the Y-type zeolites as typified by CBV-720 manufactured by Zeolyst International, and the ZSM family of zeolites as typified by ZSM-5, and ZSM-11.

All numerical ranges herein include all numerical values and ranges of all numerical values within the recited range of numerical values.

The present disclosure relates to estolide compounds, oligomeric/polymeric compounds and high-viscosity compositions thereof, and methods of making the same. In certain embodiments, the present disclosure also relates to polymeric compounds, such as estolides prepared from fatty acids having terminal sites of unsaturation, that are useful as high-viscosity oils or exhibit other unique properties (e.g., film-forming; lacquers; hardened coatings). In certain embodiments, the present disclosure relates to biosynthetic estolides having desired viscometric properties, while retaining or even improving other properties such as oxidative stability and pour point. In certain embodiments, new methods of preparing estolide compounds exhibiting such properties are provided. The present disclosure also relates to compositions comprising certain estolide compounds exhibiting such properties.

In certain embodiments are described at least one compound of Formula I:

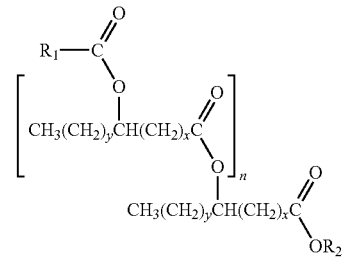

Formula I wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is an integer equal to or greater than 0;

$R_1$ is an optionally substituted alkyl that is saturated or unsaturated, and branched or unbranched; and $R_2$ is selected from hydrogen and an optionally substituted alkyl that is saturated or unsaturated, and branched or unbranched;

wherein each fatty acid chain residue of said at least one compound is independently optionally substituted, and wherein, for at least one fatty acid chain residue, x is an integer selected from 7 and 8 and y is an integer selected from 0, 1, 2, 3, 4, 5, and 6.

In certain embodiments are described at least one compound of Formula II:

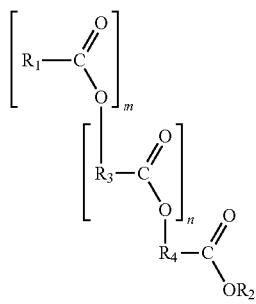

Formula II wherein m is an integer equal to or greater than 1;

n is an integer equal to or greater than 0;

$R_1$ is an optionally substituted, branched or unbranched alkyl that is saturated or unsaturated;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$, $R_3$, and $R_4$ comprises an unbranched undecanyl that is saturated or unsaturated.

In certain embodiments, the process of producing an estolide base oil comprises:

providing at least one fatty acid substrate having at least one fatty acid residue with at least one internal site of unsaturation;

providing at least one alpha olefin;

contacting the at least one fatty acid substrate with the at least one alpha olefin in the presence of a metathesis catalyst to provide an olefin product and a metathesized fatty acid product;

optionally converting the metathesized fatty acid product into at least one first fatty acid product;

optionally providing at least one second fatty acid reactant;

providing an oligomerization catalyst; and oligomerizing the metathesized fatty acid product and/or first fatty acid product, optionally with the at least one second fatty acid reactant, in the presence of the oligomerization catalyst to produce an estolide base oil.

In certain embodiments are described compounds of Formula III:

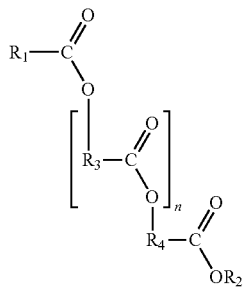

Formula III wherein n is an integer equal to or greater than 0;

$R_1$ is an optionally substituted, branched or unbranched alkyl that is saturated or unsaturated;

$R_2$ is selected from hydrogen and optionally substituted alkyl that is saturated or unsaturated, and branched or unbranched; and $R_3$ and $R_4$, independently for each occurrence, are selected from

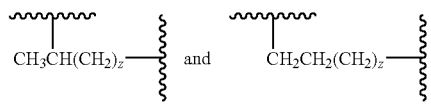

wherein $R_3$ and $R_4$ are independently optionally substituted and z is, independently for each occurrence, an integer selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40.

In certain embodiments are described a process of producing an estolide base oil, comprising:

providing at least one estolide compound having at least one fatty acid chain residue with at least one internal site of unsaturation;

providing at least one olefin reactant; and contacting the at least one estolide compound with the at least olefin reactant in the presence of a metathesis catalyst to provide an olefin product and an estolide base oil, wherein said estolide base oil comprises at least one fatty acid chain residue with at least one terminal site of unsaturation or at least one internal site of unsaturation.

A process of producing an oligomeric compound is also described. In certain embodiments, the process comprises:

providing at least one first fatty acid reactant and at least one second fatty acid reactant, wherein the at least one second fatty acid reactant has at least one terminal site of unsaturation; and reacting the at least one first fatty acid reactant with the at least one second fatty acid reactant to provide a compound, wherein a covalent bond is formed between an oxygen of a carboxylic group of the at least one first fatty acid reactant and a carbon of the at least one terminal site of unsaturation of the at least one second fatty acid reactant.

In certain embodiments, the estolides comprise at least one compound of Formula V:

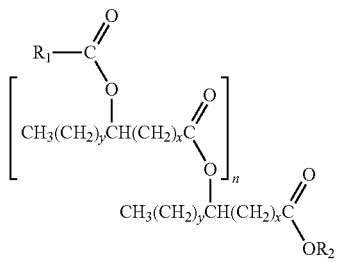

Formula V wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer equal to or greater than 0;

$R_1$ is an optionally substituted, branched or unbranched alkyl having at least one terminal site of unsaturation; and $R_2$ is selected from hydrogen and an optionally substituted alkyl that is saturated or unsaturated, and branched or unbranched, wherein each fatty acid chain residue of said at least one compound is independently optionally substituted.

In certain embodiments, the composition comprises at least one estolide of Formula I, II, or III where $R_1$ is hydrogen.

The terms "chain" or "fatty acid chain" or "fatty acid chain residue," as used with respect to the compounds of Formula I, II, III, and V, refer to one or more of the fatty acid residues incorporated in compounds, e.g., $R_3$ or $R_4$ of Formula II and III, or the structures represented by $CH_3(CH_2)_y CH(CH_2)_x C(O)O-$ in Formula I and V.

The $R_1$ in Formula I, II, III, and V at the top of each Formula shown is an example of what may be referred to as a "cap" or "capping material," as it "caps" the top of the compound. Similarly, the capping group may be an organic acid residue of general formula —OC(O)-alkyl, i.e., a carboxylic acid with a substituted or unsubstituted, saturated or unsaturated, and/or branched or unbranched alkyl as defined herein, or a formic acid residue. In certain embodiments, the "cap" or "capping group" is a fatty acid. In certain embodiments, the capping group, regardless of size, is substituted or unsubstituted, saturated or unsaturated, and/or branched or unbranched. In certain embodiments, the capping group comprises an alkyl group with at least one terminal site of unsaturation. As described in further detail below, in certain embodiments, an alkyl capping group with at least one terminal site of unsaturation may be prepared by subjecting an estolide initially having an alkyl capping group with at least one internal site of unsaturation to cross metathesis conditions. Alternatively, in certain embodiments, a compound with an alkyl capping group having at least one terminal site of unsaturation may be prepared by oligomerizing/polymerizing two or more fatty acid reactants having terminal sites of unsaturation. The cap or capping material may also be referred to as the primary or alpha (α) chain.

Depending on the manner in which the compound is synthesized, the cap or capping group alkyl may be the only alkyl from an organic acid residue in the resulting estolide that is unsaturated. In certain embodiments, it may be desirable to use a saturated organic or fatty-acid cap to increase the overall saturation of the estolide and/or to increase the resulting estolide's stability. For example, in certain embodiments, it may be desirable to provide a method of providing a saturated capped estolide by hydrogenating an unsaturated capped estolide using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials. In certain embodiments, this may be accomplished by cleaving an estolide at its internal site of unsaturation (e.g., oleic cap) with a metathesis catalyst to provide a shorter cap ($C_{10}$) having a terminal site of unsaturation. In addition, or in the alternative, as described further below, it may be desirable to add further functionalization to the compound by altering the structure of the compound at a site of unsaturation, such as altering the structure of the compound at a terminal site of unsaturation in an alkyl capping group.

The $R_4C(O)O-$ of Formula II and III, or structure $CH_3(CH_2)_y CH(CH_2)_x C(O)O-$ of Formula I and V, serve as the "base" or "base chain residue" of the estolide. Depending on the manner in which the compound is synthesized, the base organic acid or fatty acid residue may be the only residue that remains in its free-acid form after the initial synthesis of the compound. However, in certain embodiments, in an effort to alter or improve the properties of the compound, the free acid may be reacted with any number of substituents. For example, it may be desirable to react the free acid compound with alcohols, glycols, amines, or other suitable reactants to provide the corresponding ester, amide, or other reaction products. The base or base chain residue may also be referred to as tertiary or gamma (γ) chains.

The $R_3C(O)O-$ of Formula II and III, or structure $CH_3(CH_2)_y CH(CH_2)_x C(O)O-$ of Formula I and V, are linking residues that link the capping material and the base fatty-acid residue together. There may be any number of linking residues in the estolide, including when n=0 and the estolide is in its dimer form. Depending on the manner in which the compound is prepared, a linking residue may be a fatty acid and may initially be in an unsaturated form during synthesis. In some embodiments, the compound will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta (β) chains.

In certain embodiments, the cap is an acetyl group, the linking residue(s) is one or more fatty acid residues, and the base chain residue is a fatty acid residue. In certain embodiments, the linking residues present in a compound differ from one another. In certain embodiments, one or more of the linking residues differs from the base chain residue.

As noted above, in certain embodiments, suitable unsaturated fatty acids for preparing the compounds may include any mono- or polyunsaturated fatty acid. For example, monounsaturated fatty acids, along with a suitable catalyst, will form a single carbocation that allows for the addition of a second fatty acid, whereby a single link between two fatty acids is formed. Suitable monounsaturated fatty acids may include, but are not limited to, palmitoleic acid (16:1), vaccenic acid (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5). In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

The process for preparing the compounds described herein may include the use of any natural or synthetic fatty acid source. However, it may be desirable to source the fatty acids from a renewable biological feedstock. Suitable starting materials of biological origin may include plant fats, plant oils, plant waxes, animal fats, animal oils, animal waxes, fish fats, fish oils, fish waxes, algal oils and mixtures thereof. Other potential fatty acid sources may include waste and recycled food-grade fats and oils, fats, oils, and waxes obtained by genetic engineering, fossil fuel-based materials and other sources of the materials desired.

In certain embodiments, the compounds described herein may be prepared from non-naturally occurring fatty acids derived from naturally occurring feedstocks. In certain embodiments, the compounds are prepared from synthetic fatty acid products derived from naturally occurring feedstocks such as vegetable oils. For example, the synthetic fatty acid product may be prepared by cleaving fragments from larger fatty acid residues occurring in natural oils, such as triglycerides, using any of the suitable metathesis processes described further below. In certain embodiments, the resulting truncated fatty acid residue(s) may then be liberated from the glycerine backbone using any suitable hydrolytic and/or transesterification processes known to those of skill in the art. An exemplary fatty acid product includes 9-dodecenoic acid, which may be prepared via the cross metathesis of an oleic acid residue with 1-butene. In certain embodiments, the naturally-occurring fatty acid may be liberated from the glycerine backbone prior to being exposed to metathesis. Such metathesis reactions may be non-specific and produce mixtures of products, wherein reactions producing, for example, internally-unsaturated fatty acids such as 9-dodecenoic acid also produce varying amounts of the terminally-unsaturated fatty acid, 9-decenoic acid. In certain embodiments, it may be desirable to optimize the production of fatty acids having at least one terminal site of unsaturation by reacting an unsaturated fatty acid reactant (e.g., oleic acid) with ethylene under metathesis conditions, whereby the terminally-unsaturated fatty acid product (e.g., 9-decenoic acid) is produced exclusively.

In some embodiments, the compound comprises fatty-acid chains of varying lengths. In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20. In certain embodiments, for at least one fatty acid chain residue, x is an integer selected from 7 and 8.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, y is, independently for each occurrence, an integer selected from 0, 1, 2, 3, 4, 5, 6, 7, 8, 9, 10, 11, 12, 13, 14, 15, 16, 17, 18, 19, and 20. In certain embodiments, for at least one fatty acid chain residue, y is an integer selected from 7 and 8. In some embodiments, for at least one fatty acid chain residue, y is an integer selected from 0 to 6, or 1 and 2. In certain embodiments, y is, independently for each occurrence, an integer selected from 1 to 6, or 1 and 2.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y is 15. In some embodiments, x+y is, independently for each chain, an integer selected from 6, 7, 8, 9, 10, 11, 12, 13, 14, 15, 16, 17, 18, 19, 20, 21, 22, 23, and 24. In certain embodiments, x+y, independently for each chain, is an integer selected from 5 to 15. In certain embodiments, for at least one fatty acid chain residue, x+y is 7. In certain embodiments, x+y is 7 for each fatty acid chain residue. In certain embodiments, for at least one fatty acid chain residue, x+y is an integer selected from 9 to 13. In certain embodiments, for at least one fatty acid chain residue, x+y is 9. In certain embodiments, x+y is, independently for each chain, an integer selected from 9 to 13. In certain embodiments, x+y is 9 for each fatty acid chain residue.

In some embodiments, the estolide compound of Formula I, II, III, and V may comprise any number of fatty acid residues to form an "n-mer" estolide. For example, the compound may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 1, wherein said at least one compound of Formula I, II, III, and V comprises the trimer. In some embodiments, n is greater than 1. In some embodiments, n is an integer selected from 0, 1, 2, 3, 4, 5, 6, 7, 8, 9, 10, 11, 12, 13, 14, 15, 16, 17, 18, 19, and 20.

In certain embodiments, the compounds of Formula III may be larger oligomers or even polymeric in nature, wherein n is an integer selected from 1 to 1,000, 1 to 750, 1 to 500 or 1 to 100. In certain embodiments, n is an integer equal to or greater than 50, 100, 250, or even 500. In certain embodiments, n is an integer selected from 1 to 50 or 1 to 20. Without being bound to any particular theory, in certain embodiments, it is believed that compounds of Formula III have the ability to become "polymeric" in nature when they are prepared from terminally-unsaturated fatty acids, wherein the linking of fatty acids at the terminal or penultimate carbon of the fatty acid chain reduces branching and certain steric hindrances typically observed in the oligomerization of internally-unsaturated fatty acids. In certain embodiments, the stability of the carbocation at the penultimate position of a terminally-unsaturated fatty acid will provide compounds of Formula III that are linked predominantly at the penultimate carbon, such as the exemplary compound prepared in Scheme 1:

alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In certain embodiments, $R_3$ and $R_4$, independently for each occurrence, are selected from optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl

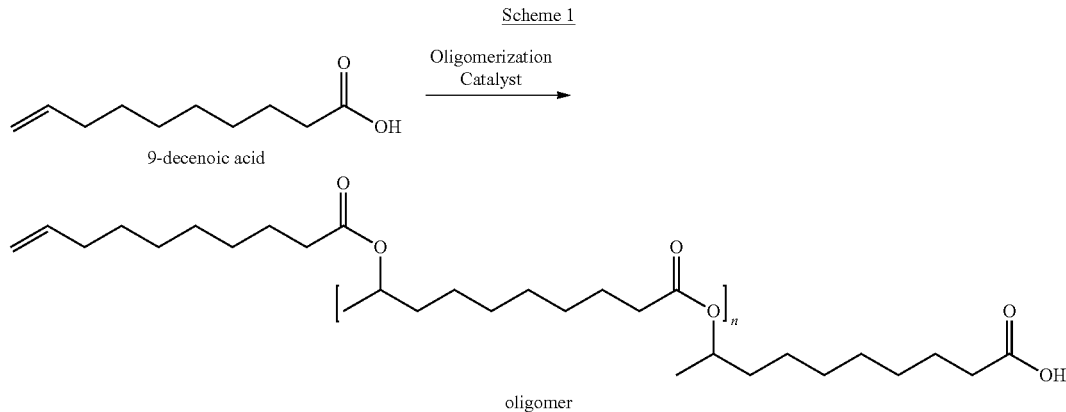

In certain embodiments, $R_1$ of Formula I, II, III, and V is an optionally substituted alkyl that is saturated or unsaturated, and branched or unbranched. In certain embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_1$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_1$ is selected from $C_{13}$ to $C_{17}$ alkyl, such as from $C_{13}$ alkyl, $C_{15}$ alkyl, and $C_{17}$ alkyl. In some embodiments, $R_1$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl. In certain embodiments, $R_1$ is an optionally substituted, branched or unbranched alkyl having at least one terminal site of unsaturation. In certain embodiments, $R_1$ is an optionally substituted, branched or unbranched alkyl having at least one terminal site of unsaturation. In certain embodiments, $R_1$ is a $C_2$ to $C_{21}$ alkyl having at least one terminal site of unsaturation.

In certain embodiments, $R_1$ is selected from the structure of Formula IV:

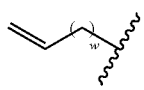

Formula IV wherein w is an integer selected from 0 to 13. In certain embodiments, w is an integer selected from 5 to 7. In certain embodiments, w is 7.

In some embodiments, $R_2$ of Formula I, II, III, and V is selected from hydrogen and an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ group is selected from $C_7$ to $C_{17}$ alkyl. In some embodiments, the alkyl group is selected from $C_7$ alkyl, $C_9$ alkyl, $C_{11}$ alkyl, $C_{13}$ alkyl, $C_{15}$ alkyl, and $C_{17}$ alkyl. In some embodiments, the alkyl group is selected from $C_{13}$ to $C_{17}$ alkyl, such as from $C_{13}$ alkyl, $C_{15}$ alkyl, and $C_{17}$ alkyl.

In certain embodiments, $R_3$ and $R_4$, independently for each occurrence, are selected from

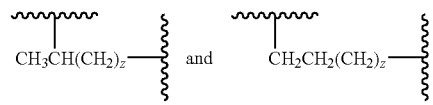

wherein $R_3$ and $R_4$ are independently optionally substituted and z is, independently for each occurrence, an integer selected from 0 to 40.

In certain embodiments, one or more of $R_3$ or $R_4$ are unsubstituted. In certain embodiments, z is, independently for each occurrence, an integer selected from 1 to 20. In certain embodiments, z is, independently for each occurrence, an integer selected from 2 to 15. In certain embodiments, z is, independently for each occurrence, an integer selected from 5 to 7. In certain embodiments, z is, independently for each occurrence, an integer selected from 1, 2, 3, 4, 5, 6, 7, 8, 9, 10, 11, 12, 13, 14, 15, 16, 17, 18, 19, and 20. In certain embodiments, z is 7.

As noted above, in certain embodiments, it may be possible to manipulate one or more of the compounds' properties by altering the length of $R_1$ and/or its degree of saturation. However, in certain embodiments, the level of substitution on $R_1$ may also be altered to change or even improve the compounds' properties. Without being bound to any particular theory, in certain embodiments, it is believed that the presence of polar substituents on $R_1$, such as one or more hydroxy groups, may increase the viscosity of the estolide, while increasing pour point. Accordingly, in some embodiments, $R_1$ will be unsubstituted or optionally substituted with a group that is not hydroxyl.

In some embodiments, the estolide is in its free-acid form, wherein $R_2$ of Formula I, II, III, or V is hydrogen. In some embodiments, $R_2$ is selected from optionally substituted alkyl that is saturated or unsaturated, and branched or unbranched. In certain embodiments, the $R_2$ residue may comprise any desired alkyl group, such as those derived from esterification of the compound with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, in certain embodiments, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl. Such groups at the $R_2$ position may be derived from esterification of the free-acid compound using the Jarcol™ line of alcohols marketed by Jarchem Industries, Inc. of Newark, N.J., including Jarcol™ I-18CG, I-20, I-12, I-16, I-18T, and 85BJ. In some cases, $R_2$ may be sourced from certain alcohols to provide branched alkyls such as isostearyl and isopalmityl. It should be understood that such isopalmityl and isostearyl alkyl groups may cover any branched variation of $C_{16}$ and $C_{18}$, respectively. For example, the compounds described herein may comprise highly-branched isopalmityl or isostearyl groups at the $R_2$ position, derived from the Fineoxocol® line of isopalmityl and isostearyl alcohols marketed by Nissan Chemical America Corporation of Houston, Tex., including Fineoxocol® 180, 180N, and 1600. Without being bound to any particular theory, in embodiments, large, highly-branched alkyl groups (e.g., isopalmityl and isostearyl) at the $R_2$ position of the estolides can provide at least one way to increase the lubricant's viscosity, while substantially retaining or even reducing its pour point.

In some embodiments, the compounds described herein may comprise a mixture of two or more compounds of Formula I, II, III, and V. It is possible to characterize the chemical makeup of an estolide, a mixture of estolides, or a composition comprising estolides, by using the compound's, mixture's, or composition's measured estolide number (EN) of compound or composition. The EN represents the average number of fatty acids added to the base fatty acid. The EN also represents the average number of estolide linkages per molecule:

EN=$n$+1 wherein n is the number of secondary (β) fatty acids. Accordingly, a single estolide compound will have an EN that is a whole number, for example for dimers, trimers, and tetramers:

dimer EN=1 trimer EN=2 tetramer EN=3

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions may comprise a mixture of two or more estolides having an EN that is an integer or fraction of an integer that is greater than 4.5, or even 5.0. In some embodiments, the EN may be an integer or fraction of an integer selected from about 1.0 to about 5.0. In some embodiments, the EN is an integer or fraction of an integer selected from 1.2 to about 4.5. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6 and 5.8. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0, 5.2, 5.4, 5.6, 5.8, and 6.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. For example, in some embodiments the estolides described herein may comprise at least one compound of Formula II:

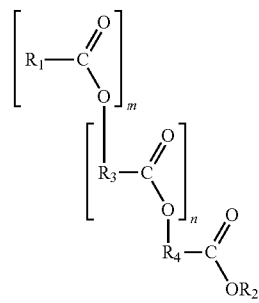

Formula II wherein m is an integer equal to or greater than 1;

n is an integer equal to or greater than 0;

$R_1$, independently for each occurrence, is an optionally substituted alkyl that is saturated or unsaturated, and branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$, $R_3$, and $R_4$ comprises an unbranched undecanyl that is saturated or unsaturated.

In certain embodiments, m is 1. In some embodiments, m is an integer selected from 2, 3, 4, and 5. In some embodiments, n is an integer selected from 1, 2, 3, 4, 5, 6, 7, 8, 9, 10, 11, and 12. In some embodiments, one or more $R_3$ differs from one or more other $R_3$ in a compound of Formula II. In some embodiments, one or more $R_3$ differs from $R_4$ in a compound of Formula II. In some embodiments, if the compounds of Formula II are prepared from one or more polyunsaturated fatty acids, it is possible that one or more of $R_3$ and $R_4$ will have one or more sites of unsaturation. In some embodiments, if the compounds of Formula II are prepared from one or more branched fatty acids, it is possible that one or more of $R_3$ and $R_4$ will be branched.

In some embodiments, $R_3$ and $R_4$ can be $CH_3(CH_2)_y CH(CH_2)_x$—, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both $R_3$ and $R_4$ are $CH_3(CH_2)_yCH(CH_2)_x$—, the compounds may be compounds according to Formula I and V.

In certain embodiments, the compounds described herein may comprise at least one compound of Formula III:

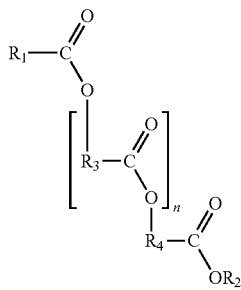

Formula III wherein n is an integer equal to or greater than 0;

$R_1$ is an optionally substituted, branched or unbranched alkyl that is saturated or unsaturated;

$R_2$ is selected from hydrogen and optionally substituted alkyl that is saturated or unsaturated, and branched or unbranched; and $R_3$ and $R_4$, independently for each occurrence, are selected from

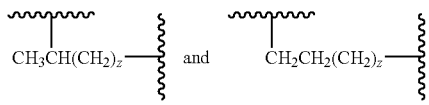

wherein $R_3$ and $R_4$ are independently optionally substituted and z is, independently for each occurrence, an integer selected from 0 to 40.

In certain embodiments, compounds of Formula III may comprise larger oligomers and, in some cases, may be considered polymeric in nature, wherein n is an integer greater than 0, such as greater than 10, 15, 20, 30, or even 50. In certain embodiments, compounds of Formula III are prepared by linking two or more fatty acids having at least one terminal site of unsaturation, wherein a covalent bond is formed between an oxygen of a carboxylic group of a first fatty acid and a carbon of a terminal site of unsaturation of a second fatty acid.

Without being bound to any particular theory, in certain embodiments, altering the EN produces estolides having desired viscometric properties while substantially retaining or even reducing pour point. For example, in some embodiments the estolides exhibit a decreased pour point upon increasing the EN value. Accordingly, in certain embodiments, a method is provided for retaining or decreasing the pour point of an estolide base oil by increasing the EN of the base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil is accomplished by distillation, chromatography, membrane separation, phase separation, affinity separation, solvent extraction, or combinations thereof. In some embodiments, the distillation takes place at a temperature and/or pressure that is suitable to separate the estolide base oil into different "cuts" that individually exhibit different EN values. In some embodiments, this may be accomplished by subjecting the base oil temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

In some embodiments, the compounds and compositions exhibit an EN that is greater than or equal to 1, such as an integer or fraction of an integer selected from about 1.0 to about 2.0. In some embodiments, the EN is an integer or fraction of an integer selected from about 1.0 to about 1.6. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, and 1.9. In some embodiments, the EN is selected from a value less than 1.1, 1.2, 1.3, 1.4, 1.5, 1.6, 1.7, 1.8, 1.9, and 2.0.

In some embodiments, the EN is greater than or equal to 1.5, such as an integer or fraction of an integer selected from about 1.8 to about 2.8. In some embodiments, the EN is an integer or fraction of an integer selected from about 2.0 to about 2.6. In some embodiments, the EN is a fraction of an integer selected from about 2.1 to about 2.5. In some embodiments, the EN is selected from a value greater than 1.8, 1.9, 2.0, 2.1, 2.2, 2.3, 2.4, 2.5, 2.6, and 2.7. In some embodiments, the EN is selected from a value less than 1.9, 2.0, 2.1, 2.2, 2.3, 2.4, 2.5, 2.6, 2.7, and 2.8. In some embodiments, the EN is about 1.8, 2.0, 2.2, 2.4, 2.6, or 2.8.

In some embodiments, the EN is greater than or equal to about 4, such as an integer or fraction of an integer selected from about 4.0 to about 5.0. In some embodiments, the EN is a fraction of an integer selected from about 4.2 to about 4.8. In some embodiments, the EN is a fraction of an integer selected from about 4.3 to about 4.7. In some embodiments, the EN is selected from a value greater than 4.0, 4.1, 4.2, 4.3, 4.4, 4.5, 4.6, 4.7, 4.8, and 4.9. In some embodiments, the EN is selected from a value less than 4.1, 4.2, 4.3, 4.4, 4.5, 4.6, 4.7, 4.8, 4.9, and 5.0. In some embodiments, the EN is about 4.0, 4.2, 4.4, 4.6, 4.8, or 5.0.

In some embodiments, the EN is greater than or equal to about 5, such as an integer or fraction of an integer selected from about 5.0 to about 6.0. In some embodiments, the EN is a fraction of an integer selected from about 5.2 to about 5.8. In some embodiments, the EN is a fraction of an integer selected from about 5.3 to about 5.7. In some embodiments, the EN is selected from a value greater than 5.0, 5.1, 5.2, 5.3, 5.4, 5.5, 5.6, 5.7, 5.8, and 5.9. In some embodiments, the EN is selected from a value less than 5.1, 5.2, 5.3, 5.4, 5.5, 5.6, 5.7, 5.8, 5.9, and 6.0. In some embodiments, the EN is about 5.0, 5.2, 5.4, 5.4, 5.6, 5.8, or 6.0.

In some embodiments, the EN is greater than or equal to 1, such as an integer or fraction of an integer selected from about 1.0 to about 2.0. In some embodiments, the EN is a fraction of an integer selected from about 1.1 to about 1.7. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, or 1.9. In some embodiments, the EN is selected from a value less than 1.2, 1.3, 1.4, 1.5, 1.6, 1.7, 1.8, 1.9, or 2.0. In some embodiments, the EN is about 1.0, 1.2, 1.4, 1.6, 1.8, or 2.0. In some embodiments, the EN is greater than or equal to 1, such as an integer or fraction of an integer selected from about 1.2 to about 2.2. In some embodiments, the EN is an integer or fraction of an integer selected from about 1.4 to about 2.0. In some embodiments, the EN is a fraction of an integer selected from about 1.5 to about 1.9. In some embodiments, the EN is selected from a value greater than 1.0, 1.1, 1.2, 1.3, 1.4, 1.5, 1.6, 1.7, 1.8, 1.9, 2.0, and 2.1. In some embodiments, the EN is selected from a value less than 1.2, 1.3, 1.4, 1.5, 1.6, 1.7, 1.8, 1.9, 2.0, 2.1, and 2.2. In some embodiments, the EN is about 1.0, 1.2, 1.4, 1.6, 1.8, 2.0, or 2.2.

In some embodiments, the EN is greater than or equal to 2, such as an integer or fraction of an integer selected from about 2.8 to about 3.8. In some embodiments, the EN is an integer or fraction of an integer selected from about 2.9 to about 3.5. In some embodiments, the EN is an integer or fraction of an integer selected from about 3.0 to about 3.4. In some embodiments, the EN is selected from a value greater than 2.0, 2.1, 2.2., 2.4, 2.5, 2.6, 2.7, 2.8, 2.9, 3.0, 3.1, 3.4, 3.5, 3.6, and 3.7. In some embodiments, the EN is selected from a value less than 2.2, 2.3, 2.4, 2.5, 2.6, 2.7, 2.8, 2.9, 3.0, 3.1, 3.2, 3.3, 3.4, 3.5, 3.6, 3.7, and 3.8. In some embodiments, the EN is about 2.0, 2.2, 2.4, 2.6, 2.8, 3.0, 3.2, 3.4, 3.6, or 3.8. Typically, base stocks and lubricant compositions exhibit certain lubricity, viscosity, and/or pour point characteristics. For example, in certain embodiments, suitable viscosity characteristics of the base oil may range from about 10 cSt to about 250 cSt at 40° C., and/or about 3 cSt to about 30 cSt at 100° C. In some embodiments, the compounds and compositions may exhibit viscosities within a range from about 50 cSt to about 150 cSt at 40° C., and/or about 10 cSt to about 20 cSt at 100° C.

In some embodiments, the estolide compounds and compositions may exhibit viscosities less than about 55 cSt at 40° C. or less than about 45 cSt at 40° C., and/or less than about 12 cSt at 100° C. or less than about 10 cSt at 100° C. In some embodiments, the estolide compounds and compositions may exhibit viscosities within a range from about 25 cSt to about 55 cSt at 40° C., and/or about 5 cSt to about 11 cSt at 100° C. In some embodiments, the estolide compounds and compositions may exhibit viscosities within a range from about 35 cSt to about 45 cSt at 40° C., and/or about 6 cSt to about 10 cSt at 100° C. In some embodiments, the estolide compounds and compositions may exhibit viscosities within a range from about 38 cSt to about 43 cSt at 40° C., and/or about 7 cSt to about 9 cSt at 100° C.

In some embodiments, the estolide compounds and compositions may exhibit viscosities less than about 120 cSt at 40° C. or less than about 100 cSt at 40° C., and/or less than about 18 cSt at 100° C. or less than about 17 cSt at 100° C. In some embodiments, the estolide compounds and compositions may exhibit a viscosity within a range from about 70 cSt to about 120 cSt at 40° C., and/or about 12 cSt to about 18 cSt at 100° C. In some embodiments, the estolide compounds and compositions may exhibit viscosities within a range from about 80 cSt to about 100 cSt at 40° C., and/or about 13 cSt to about 17 cSt at 100° C. In some embodiments, the estolide compounds and compositions may exhibit viscosities within a range from about 85 cSt to about 95 cSt at 40° C., and/or about 14 cSt to about 16 cSt at 100° C.

In some embodiments, the estolide compounds and compositions may exhibit viscosities greater than about 180 cSt at 40° C. or greater than about 200 cSt at 40° C., and/or greater than about 20 cSt at 100° C. or greater than about 25 cSt at 100° C. In some embodiments, the estolide compounds and compositions may exhibit a viscosity within a range from about 180 cSt to about 230 cSt at 40° C., and/or about 25 cSt to about 31 cSt at 100° C. In some embodiments, estolide compounds and compositions may exhibit viscosities within a range from about 200 cSt to about 250 cSt at 40° C., and/or about 25 cSt to about 35 cSt at 100° C. In some embodiments, estolide compounds and compositions may exhibit viscosities within a range from about 210 cSt to about 230 cSt at 40° C., and/or about 28 cSt to about 33 cSt at 100° C. In some embodiments, the estolide compounds and compositions may exhibit viscosities within a range from about 200 cSt to about 220 cSt at 40° C., and/or about 26 cSt to about 30 cSt at 100° C. In some embodiments, the estolide compounds and compositions may exhibit viscosities within a range from about 205 cSt to about 215 cSt at 40° C., and/or about 27 cSt to about 29 cSt at 100° C.

In some embodiments, the estolide compounds and compositions may exhibit viscosities less than about 45 cSt at 40° C. or less than about 38 cSt at 40° C., and/or less than about 10 cSt at 100° C. or less than about 9 cSt at 100° C. In some embodiments, the estolide compounds and compositions may exhibit a viscosity within a range from about 20 cSt to about 45 cSt at 40° C., and/or about 4 cSt to about 10 cSt at 100° C. In some embodiments, the estolide compounds and compositions may exhibit viscosities within a range from about 28 cSt to about 38 cSt at 40° C., and/or about 5 cSt to about 9 cSt at 100° C. In some embodiments, the estolide compounds and compositions may exhibit viscosities within a range from about 30 cSt to about 35 cSt at 40° C., and/or about 6 cSt to about 8 cSt at 100° C.

In some embodiments, the estolide compounds and compositions may exhibit viscosities less than about 80 cSt at 40° C. or less than about 70 cSt at 40° C., and/or less than about 14 cSt at 100° C. or less than about 13 cSt at 100° C. In some embodiments, the estolide compounds and compositions may exhibit a viscosity within a range from about 50 cSt to about 80 cSt at 40° C., and/or about 8 cSt to about 14 cSt at 100° C. In some embodiments, the estolide compounds and compositions may exhibit viscosities within a range from about 60 cSt to about 70 cSt at 40° C., and/or about 9 cSt to about 13 cSt at 100° C. In some embodiments, the estolide compounds and compositions may exhibit viscosities within a range from about 63 cSt to about 68 cSt at 40° C., and/or about 10 cSt to about 12 cSt at 100° C.

In some embodiments, the estolide compounds and compositions may exhibit viscosities greater than about 120 cSt at 40° C. or greater than about 130 cSt at 40° C., and/or greater than about 15 cSt at 100° C. or greater than about 18 cSt at 100° C. In some embodiments, the estolide compounds and compositions may exhibit a viscosity within a range from about 120 cSt to about 150 cSt at 40° C., and/or about 16 cSt to about 24 cSt at 100° C. In some embodiments, the estolide compounds and compositions may exhibit viscosities within a range from about 130 cSt to about 160 cSt at 40° C., and/or about 17 cSt to about 28 cSt at 100° C. In some embodiments, the estolide compounds and compositions may exhibit viscosities within a range from about 130 cSt to about 145 cSt at 40° C., and/or about 17 cSt to about 23 cSt at 100° C. In some embodiments, the estolide compounds and compositions may exhibit viscosities within a range from about 135 cSt to about 140 cSt at 40° C., and/or about 19 cSt to about 21 cSt at 100° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, or 400 cSt. at 40° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 cSt at 100° C. In certain embodiments, estolides may exhibit desirable low-temperature pour point properties. In some embodiments, the estolide compounds and compositions may exhibit a pour point lower than about −25° C., about −35° C., −40° C., or even about −50° C. In some embodiments, the estolide compounds and compositions have a pour point of about −25° C. to about −45° C. In some embodiments, the pour point falls within a range of about −30° C. to about −40° C., about −34° C. to about −38° C., about −30° C. to about −45° C., −35° C. to about −45° C., 34° C. to about −42° C., about −38° C. to about −42° C., or about 36° C. to about −40° C. In some embodiments, the pour point falls within the range of about −27° C. to about −37° C., or about −30° C. to about −34° C. In some embodiments, the pour point falls within the range of about −25° C. to about −35° C., or about −28° C. to about −32° C. In some embodiments, the pour point falls within the range of about −28° C. to about −38° C., or about −31° C. to about −35° C. In some embodiments, the pour point falls within the range of about −31° C. to about −41° C., or about −34° C. to about −38° C. In some embodiments, the pour point falls within the range of about −40° C. to about −50° C., or about −42° C. to about −48° C. In some embodiments, the pour point falls within the range of about −50° C. to about −60° C., or about −52° C. to about −58° C. In some embodiments, the upper bound of the pour point is less than about −35° C., about −36° C., about −37° C., about −38° C., about −39° C., about −40° C., about −41° C., about −42° C., about −43° C., about −44° C., or about −45° C. In some embodiments, the lower bound of the pour point is greater than about −70° C., about −69° C., about −68° C., about −67° C., about −66° C., about −65° C., about −64° C., about −63° C., about −62° C., about −61° C., about −60° C., about −59° C., about −58° C., about −57° C., about −56° C., −55° C., about −54° C., about −53° C., about −52° C., −51, about −50° C., about −49° C., about −48° C., about −47° C., about −46° C., or about −45° C.

In addition, in certain embodiments, the compounds may exhibit decreased Iodine Values (IV) when compared to compounds prepared by other methods. IV is a measure of the degree of total unsaturation of an oil, and is determined by measuring the amount of iodine per gram of estolide (eg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of the compounds in an effort to increase the compound's oxidative stability, while also decreasing harmful deposits and the corrosiveness of the compound.

In some embodiments, compounds and compositions described herein have an IV of less than about 40 cg/g or less than about 35 cg/g. In some embodiments, the compounds have an IV of less than about 30 cg/g, less than about 25 cg/g, less than about 20 cg/g, less than about 15 cg/g, less than about 10 cg/g, or less than about 5 cg/g. The IV of a composition may be reduced by decreasing the compound's degree of unsaturation. This may be accomplished by, for example, by increasing the amount of saturated capping materials relative to unsaturated capping materials when synthesizing the compounds. Alternatively, in certain embodiments, IV may be reduced by hydrogenating compounds having unsaturated caps.

In certain embodiments, the estolides described herein may be prepared from non-naturally occurring fatty acid starting materials. In certain embodiments, the fatty acid starting materials may be derived through the cross metathesis of naturally-occurring fatty acid residues. In certain embodiments, the estolides are prepared through the process comprising:

providing at least one fatty acid substrate;
providing at least one alpha olefin;
contacting the at least one fatty acid substrate with the at least one alpha olefin in the presence of a metathesis catalyst to provide an olefin product and a metathesized fatty acid product;
optionally converting the metathesized fatty acid product into at least one first fatty acid product;
optionally providing at least one second fatty acid reactant;
providing an oligomerization catalyst; and
oligomerizing the metathesized fatty acid product and/or first fatty acid product, optionally with the at least one second fatty acid reactant, in the presence of the oligomerization catalyst to produce an estolide base oil.

In certain embodiments, the fatty acid substrate is a compound or composition comprising at least one fatty acid residue. In certain embodiments, the fatty acid substrate comprises at least one internal site of unsaturation, wherein said site of unsaturation is not at the terminus (i.e., alpha position) of the at least one of the fatty acid residue of said fatty acid substrate. In certain embodiments, the at least one site of unsaturation is a double bond, such as the double bond at the 9 position of oleic acid, the double bonds at the 9 and 12 position of linoleic acid, or the double bonds at the 9, 12, and 15 positions of linolenic acid. In certain embodiments, the at least one fatty acid substrate is selected from unsaturated fatty acids, unsaturated fatty acid esters (e.g., alkyl esters and glycerides), and unsaturated fatty acid oligomers. In certain embodiments, the at least one fatty acid substrate is selected from monoglycerides, diglycerides, and triglycerides. In certain embodiments, the at least one fatty acid substrate comprises one or more fatty acids or fatty acid alkyl esters derived from monoglycerides, diglycerides, or triglycerides via hydrolysis and transesterification, respectively.

In certain embodiments, the at least one fatty acid substrate is contacted with at least one alpha olefin in the presence of a metathesis catalyst to provide an olefin product and a metathesized fatty acid product. In certain embodiments, the olefin product is a terminal olefin and/or an internal olefin. For example, a fatty acid triglyceride comprising an oleic acid residue may be contacted with an alpha olefin such as 1-butene in the presence of a metathesis catalyst to provide, inter alia, a metathesized fatty acid product (triglyceride comprising a 9-dodecenoic acid residue) and a terminal olefin (1-decene), as shown in Scheme 2:

Scheme 2

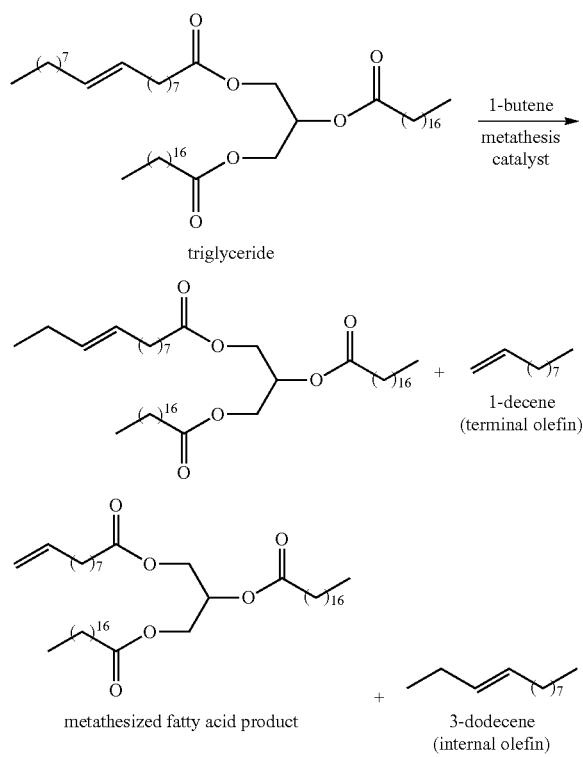

triglyceride metathesized fatty acid product 1-decene (terminal olefin)

3-dodecene (internal olefin)

In certain embodiments, the resulting metathesized fatty acid product(s) is converted into at least one first fatty acid product. For example, it may be desirable to convert the triglyceride comprising a 9-dodecenoic acid residue (metathesized fatty acid product) into 9-dodecenoic acid (first fatty acid product) by subjecting the triglyceride to hydrolysis conditions, as shown in Scheme 3:

Scheme 3

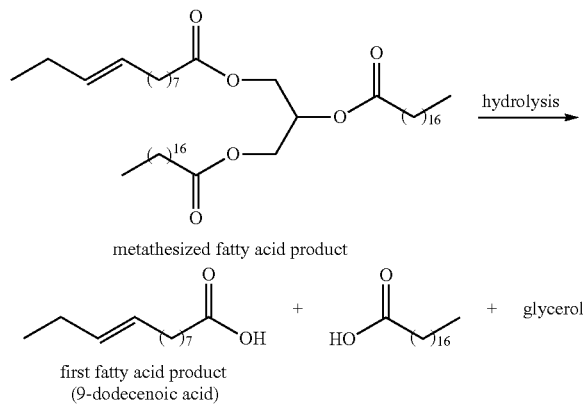

metathesized fatty acid product first fatty acid product (9-dodecenoic acid)

Alternatively, it may be desirable to convert the triglyceride comprising a 9-dodecenoic acid residue (metathesized fatty acid product) into a 9-dodecenoic acid ester (first fatty acid product) by subjecting the triglyceride to transesterification conditions in the presence of an alcohol (e.g., methanol). Exemplary processes include the one set forth in Scheme 4:

Scheme 4

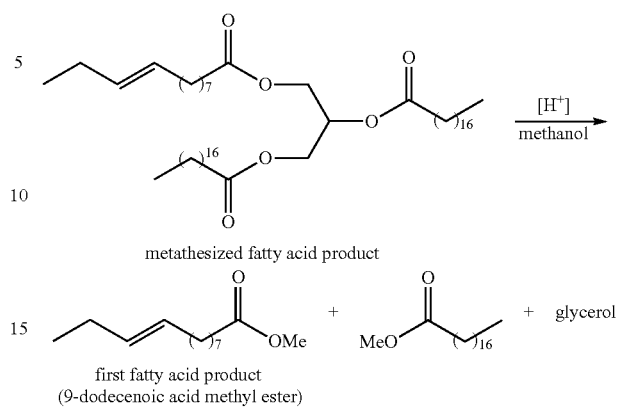

metathesized fatty acid product first fatty acid product (9-dodecenoic acid methyl ester)

Suitable hydrolysis and transesterification conditions include any of the methods known to persons of ordinary skill in the art, such as acid-catalyzed and/or Lewis Acid-catalyzed conditions. In certain embodiments, the at least one fatty acid substrate will comprise a free fatty acid, which may be reacted with an alpha olefin to provide a metathesized fatty acid product that is also a free fatty acid. Thus, in certain embodiments, the optional converting of the metathesized fatty acid product into at least one first fatty acid product is not undertaken.

In certain embodiments, the at least one fatty acid substrate may be reacted with at least one alpha olefin, such as alpha olefin cross-metathesis compound. In certain embodiments, the at least one alpha olefin may comprise more than 2 carbons, such as from 2 to 20 carbons. In certain embodiments, the at least one fatty acid substrate is reacted with ethene to provide a metathesized fatty acid product having a fatty acid residue with at least one terminal site of unsaturation. In certain embodiments, the alpha olefin comprises 3 or more carbons, such as from 3 to 10 carbons. In certain embodiments, reacting the at least one fatty acid substrate with an alpha olefin comprising 3 or more carbons provides a metathesized fatty acid product comprising at least one internal site of unsaturation.

Exemplary alpha olefins include, but are not limited to, ethene, propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene and larger alpha olefins, 2-propenol, 3-butenol, 4-pentenol, 5-hexenol, 6-heptenol, 7-octenol, 8-nonenol, 9-decenol, 10-undecenol, 11-dodecenol, 12-tridecenol, 13-tetradecenol, 14-pentadecenol, 15-hexadecenol, 16-heptadecenol, 17-octadecenol, 18-nonadecenol, 19-eicosenol and larger alpha alkenols, 2-propenyl acetate, 3-butenyl acetate, 4-pentenyl acetate, 5-hexenyl acetate, 6-heptenyl acetate, 7-octenyl acetate, 8-nonenyl acetate, 9-decenyl acetate, 10-undecenyl acetate, 11-dodecenyl acetate, 12-tridecenyl acetate 13-tetradecenyl acetate, 14-pentadecenyl acetate, 15-hexadecenyl acetate, 16-heptadecenyl acetate, 17-octadecenyl acetate, 18-nonadecenyl acetate, 19-eicosenyl acetate and larger alpha-alkenyl acetates, 2-propenyl chloride, 3-butenyl chloride, 4-pentenyl chloride, 5-hexenyl chloride, 6-heptenyl chloride, 7-octenyl chloride, 8-nonenyl chloride, 9-decenyl chloride, 10-undecenyl chloride, 11-dodecenyl chloride, 12-tridecenyl chloride, 13-tetradecenyl chloride, 14-pentadecenyl chloride, 15-hexadecenyl chloride, 16-heptadecenyl chloride, 17-octadecenyl chloride, 18-nonadecenyl chloride, 19-eicosenyl chloride and larger alpha-alkenyl chlorides, bromides, and iodides, allyl cyclohexane, allyl cyclopentane, and the like. Exemplary disubstituted alpha-olefins include, but are not limited to, isobutylene, 2-methylbut-1-ene, 2-methylpent-1-ene, 2-methylhex-1-ene, 2-methylhept-1-ene, 2-methyloct-1-ene, and the like.

In certain embodiments, the at least one alpha olefin is selected from propene, 1-butene, 1-pentene, 1-hexene, 1-heptene, and 1-octene. In certain embodiments, the at least one first fatty acid substrate is reacted with at least one alpha olefin having 3 or more carbons to provide a metathesized fatty acid product having a fatty acid residue with at least one internal site of unsaturation.

In certain embodiments, the reactions described comprise reaction components that include at least one fatty acid substrate and at least one alpha olefin. In certain embodiments, the reaction components may be solid, liquid, or gaseous. In certain embodiments, the reaction can be carried out under conditions to ensure the at least one fatty acid substrate and the at least one alpha olefin are liquid. In certain embodiments, the use of a liquid cross-metathesis partner instead of a gaseous alpha olefin (e.g., ethylene) may allow for the convenient controlling of reaction pressures, and may reduce or eliminate the need for vapor condensers and vapor reclaiming equipment.

In certain embodiments, the at least one alpha olefin is soluble in the at least one fatty acid substrate. In certain embodiments, the at least one alpha olefin may have a solubility of at least 0.25 M, at least 1 M, at least 3 M, or at least 5 M in the at least one fatty acid substrate. In certain embodiments, the at least one alpha olefin has a low solubility in the at least one fatty acid substrate, and the cross-metathesis reaction occurs as an interfacial reaction. In certain embodiments, the at least one alpha olefin may be provided in the form of a gas. In certain embodiments, the pressure of a gaseous alpha olefin over the reaction solution is maintained in a range that has a minimum of about 10 psig, 15 psig, 50 psig, or 80 psig, and a maximum of about 250 psig, 200 psig, 150 psig, or 130 psig.

In certain embodiments, the metathesis reaction is catalyzed by any suitable cross-metathesis catalysts known to persons of skill in the art. In certain embodiments, the catalyst is added to the reaction medium as a solid, but may also be added as a solution wherein the catalyst is dissolved in an appropriate solvent. In certain embodiments, the catalyst loading will depend on a variety of factors such as the identity of the reactants and the reaction conditions that are employed. In certain embodiments, the catalyst will be present in an amount that ranges from about 0.1 ppm, 1 ppm, or 5 ppm, to about 10 ppm, 15 ppm, 25 ppm, 50 ppm, 100 ppm, 200 ppm, 500 ppm, or 1000 ppm relative to the amount of the at least one fatty acid substrate. Catalyst loading, when measured in ppm relative to the amount of the at least one fatty acid substrate, may be calculated using the equation $$\text{ppm catalyst} = \frac{\text{moles catalyst}}{\text{moles fatty acid substrate double bonds}} * 1{,}000{,}000$$

In certain embodiments, the amount of catalyst is measured in terms of mol % relative to the amount of the at least one fatty acid substrate, using the equation $$\text{mol \% catalyst} = \frac{\text{moles catalyst}}{\text{moles fatty acid substrate double bonds}} * 100$$

Thus, in certain embodiments, the metathesis catalyst is present in an amount that ranges from about 0.00001 mol %, 0.0001 mol %, or 0.0005 mol %, to about 0.001 mol %, 0.0015 mol %, 0.0025 mol %, 0.005 mol %, 0.01 mol %, 0.02 mol %, 0.05 mol %, or 0.1 mol % relative to the at least one fatty acid substrate.

In certain embodiments, the cross metathesis is carried out under a dry, inert atmosphere. Such an atmosphere may be created using any inert gas, including such gases as nitrogen and argon. In certain embodiments, the use of an inert atmosphere may be optimal in terms of promoting catalyst activity, and reactions performed under an inert atmosphere may be performed with relatively low catalyst loading. In certain embodiments, the reactions of the may also be carried out in an oxygen-containing and/or a water-containing atmosphere, and in certain embodiments, the reactions are carried out under ambient conditions. In certain embodiments, the presence of oxygen, water, or other impurities in the reaction may necessitate the use of higher catalyst loadings as compared with reactions performed under an inert atmosphere.

In certain embodiments, the metathesis catalyst comprises one or more compounds selected from alkylidene methathesis catalysts, such as osmium and ruthenium alkylidene catalysts. In certain embodiments, the metathesis catalyst is selected from one or more compounds of Formula A:

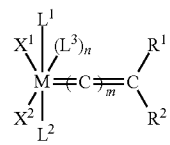

Formula A wherein
M is a Group 8 transition metal;
$L^1$, $L^2$ and $L^3$ are independently selected from optionally substituted alkyl, optionally substituted aryl, optionally substituted heteroaryl (e.g., imidazole, pyrazine, pyridine, pyrrole), optionally substituted heterocycloalkyl (e.g., imidazolidine, pyrazolidine), phosphine, sulfonated phosphine, phosphite, phosphonite, arsine, optionally substituted amine, sulfoxide, nitrosyl, and thioether;
n is 0 or 1;
m is 0, 1 or 2;
$X^1$ and $X^2$ are independently selected from hydrogen, halogen (e.g., chlorine), optionally substituted alkyl, optionally substituted alkoxy, optionally substituted aryl, optionally substituted heteroaryl, optionally substituted heterocycloalkyl; and
$R^1$ and $R^2$ are independently selected from hydrogen and optionally substituted alkyl, optionally substituted aryl, optionally substituted heteroaryl, and optionally substituted heterocycloalkyl, wherein any two or more of $X^1$, $X^2$, $L^1$, $L^2$, $L^3$, $R^1$ and $R^2$ can optionally taken together to form a cyclic or heterocyclic group, and wherein further any one or more of $X^1$, $X^2$, $L^1$, $L^2$, $L^3$, $R^1$ and $R^2$ may be attached to a support.

Exemplary metathesis catalysts include, but are not limited to, alkylidene catalysts generally known as first and second generation Grubbs' catalysts. Other exemplary catalysts and methods of making the same may include those described in Schwab et al. (1996) J. Am. Chem. Soc. 118:100-110; Scholl et al. (1999) Org. Lett. 6:953-956; Sanford et al. (2001) J. Am. Chem. Soc. 123:749-750; U.S. Pat. No. 5,312,940; U.S. Pat. No. 5,342,909; U.S. Patent Publication No. 2003/0055262 to Grubbs et al. filed Apr. 16, 2002; International Patent Publication No. WO 02/079208; International Patent Publication No. WO 03/11455A1 to Grubbs et al. published Feb. 13, 2003, all of which are incorporated by reference in their entireties for all purposes.

As described above, the at least one fatty acid substrate can be metathesized to provide a metathesized fatty acid product. In certain embodiments, the metathesis leaves the fatty acid substrate substantially intact and/or unchanged, but for the cleavage and shortening of the at least one fatty acid residue of said fatty acid substrate. For example, in certain embodiments, the metathesis of a diglyceride comprising an oleic acid residue with 1-butene will provide a diglyceride comprising a 9-dodecenoic acid residue, as well as a cleaved 1-decene terminal olefin. In certain embodiments, the cross metathesis of the at least one fatty acid substrate provides a mixture of multiple products. For example, the cross metathesis of the methyl ester of oleic acid may provide a mixture of 1-decene, 3-dodecene, 9-dodecenoic acid methyl ester, and 9-decenoic acid methyl ester.

In certain embodiments, the metathesized fatty acid product and/or first fatty acid product are independently selected from unsaturated fatty acids, unsaturated fatty acid esters, and unsaturated fatty acid oligomers. In some embodiments, the at least one second fatty acid reactant is selected from saturated and unsaturated fatty acids and saturated and unsaturated fatty acid oligomers.

In certain embodiments, the process of producing an estolide base oil comprises oligomerizing the at least one second fatty acid reactant with the metathesized fatty acid product and/or fatty acid product in the presence of an oligomerization catalyst. In certain embodiments, the process comprises the oligomerization of one or more free fatty acids.

In certain embodiments, when the at least one first fatty acid substrate comprises an unsaturated free fatty acid, the resulting metathesized fatty acid product is also a free fatty acid and is not converted into at least one first fatty acid product. Thus, in certain embodiments, the metathesized fatty acid product is oligomerized to provide an estolide base oil. In certain embodiments, the metathesized fatty acid product may be oligomerized with at least one second fatty acid reactant.

In certain embodiments, the oligomerizing of the metathesized fatty acid product and/or first fatty acid product, optionally with the at least one second fatty acid reactant, will result in the production of a free fatty acid oligomer. For example, metathesis of at least one first fatty acid substrate that comprises an oleic acid residue-containing triglyceride will result in a 9-dodecenoic acid residue-containing triglyceride metathesized fatty acid product. Hydrolysis of that metathesized fatty acid product will result in 9-dodecenoic acid (first fatty acid product), which can subsequently be oligomerized by itself and/or with at least one second fatty acid reactant (e.g., oleic acid, 9-decenoic acid) to provide a free fatty acid oligomer (estolide base oil). Alternatively, transesterification of the metathesized fatty acid product with an alcohol will provide a 9-dodecenoic acid ester (first fatty acid product), which can subsequently be contacted with at least one second fatty acid reactant (e.g., oleic acid, 9-dodecenoic acid) to provide the esterified estolide. In certain embodiments, when the first fatty acid product is an ester, the resulting esterified estolide will exist predominantly in its dimer form (isomers possible). Exemplary processes include those set forth in Scheme 5:

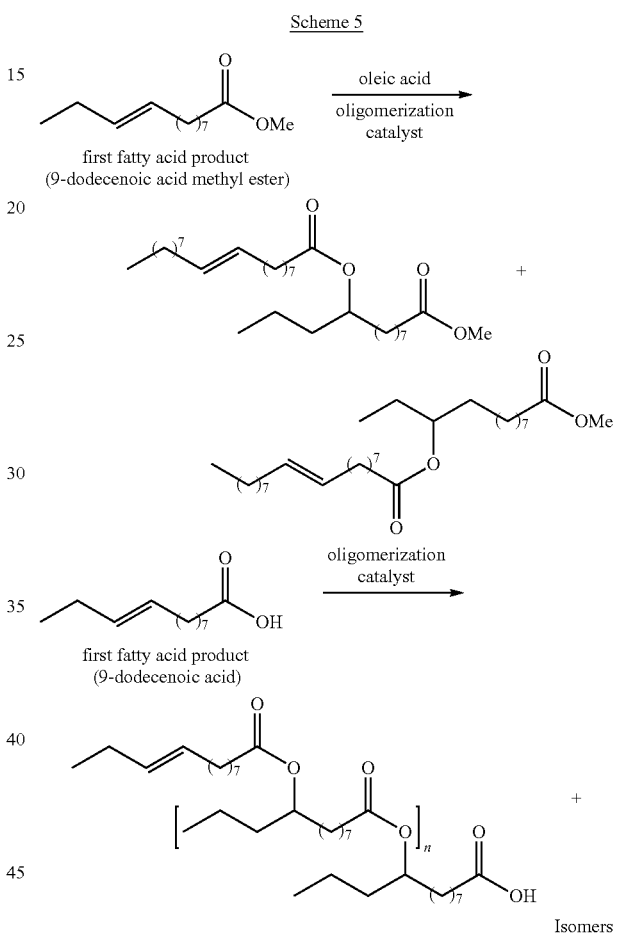

In certain embodiments, the resulting estolide base oil is in its free-acid form, wherein the base fatty acid residue is unesterified (e.g., $R_2$ is hydrogen for compounds of Formula I). Accordingly, in certain embodiments, the process further comprises esterifying the estolide base oil with an alcohol to provide an esterified estolide base oil. Exemplary esterification methods include those set forth below in Scheme 9.

In certain embodiments, the process of producing the estolide base oil comprises
    providing at least one fatty acid substrate having at least one fatty acid residue with at least one internal site of unsaturation;
    providing at least one alpha olefin;
    contacting the at least one fatty acid substrate with the at least one alpha olefin in the presence of a metathesis catalyst to provide an olefin product and a metathesized fatty acid product;
    optionally providing at least one second fatty acid reactant;

providing an oligomerization catalyst; and
oligomerizing the metathesized fatty acid product, optionally with the at least one second fatty acid reactant, in the presence of the oligomerization catalyst to produce an estolide base oil In certain embodiments, the at least one fatty acid substrate, at least one alpha olefin, metathesis catalyst, metathesized fatty acid product, oligomerization catalyst, and the optional at least one second fatty acid reactant may comprise any of the compounds and compositions previously described herein. In certain embodiments, the at least one first fatty acid substrate is selected from unsaturated fatty acids and unsaturated fatty acid esters. In certain embodiments, the at least one alpha olefin is selected from ethylene, propene, 1-butene, 1-pentene, 1-hexene, 1-heptene, and 1-octene. In certain embodiments, the metathesis catalyst is an osmium or ruthenium alkylidene metathesis catalyst.

In certain embodiments, the at least one fatty acid substrate comprises at least one fatty acid residue selected from oleic acid, linoleic acid, and linolenic acid. In certain embodiments, the at least one fatty acid substrate is an unsaturated fatty acid. In certain embodiments, the metathesized fatty acid product comprises an unsaturated fatty acid. In certain embodiments, the metathesized fatty acid product comprises a mixture of a fatty acid having a terminal site of unsaturation (e.g., 9-decenoic acid) and a fatty acid having an internal site of unsaturation (e.g., 9-dodecenoic acid). In certain embodiments, the olefin product comprises a mixture of a terminal olefin (e.g., 1-decene) and an internal olefin (e.g., 3-dodecene). In certain embodiments, the metathesized fatty acid product is a terminal fatty acid such as 9-decenoic acid, and the at least one internal olefin such as 3-dodecene. In certain embodiments, the metathesized fatty acid product is a terminal fatty acid such as 9-decenoic acid, and the olefin product is a terminal olefin such as 1-decene. An exemplary process includes the one set forth in Scheme 6:

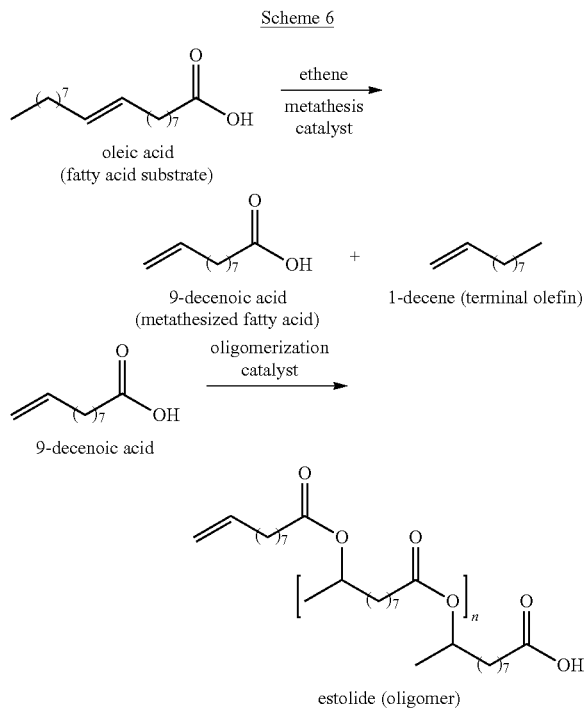

In certain embodiments, the resulting estolide base oil is in its free-acid form, wherein the base fatty acid residue is unesterified (e.g., $R_2$ is hydrogen for compounds of Formula III). Accordingly, in certain embodiments, the process further comprises esterifying the estolide base oil with an alcohol to provide an esterified estolide base oil.

In certain embodiments, the estolides described herein may be prepared from naturally occurring fatty acid starting materials. However, in certain embodiments, it may be desirable to alter the structure of the estolide in an effort to improve its properties. As noted above, in certain embodiments, estolides comprises shorter fatty acid caps may provide desirable cold-temperature properties. Accordingly, in certain embodiments, the process for producing the estolide comprises:
  providing at least one estolide compound having at least one fatty acid chain residue with at least one internal site of unsaturation;
  providing at least one alpha olefin; and
  contacting the at least one estolide compound with the at least one alpha olefin in the presence of a metathesis catalyst to provide an olefin product and an estolide base oil, wherein said estolide base oil comprises at least one fatty acid chain residue with at least one terminal site of unsaturation or at least one internal site of unsaturation.

In certain embodiments, the at least one estolide compound is prepared by any of the processes described herein, such as the oligomerization of oleic acid. In certain embodiments, the resulting at least one estolide compound will comprise at least one fatty acid residue having at least one internal site of unsaturation. For example, the oligomerization of oleic acid molecules will result in an estolide having an oleic-acid (oleate) cap. In certain embodiments, it may be desirable to remove the internal site of unsaturation by subjecting the at least one estolide compound to cross metathesis conditions, wherein the resulting oleic estolide comprises a truncated alkyl cap (i.e., $C_{10}$ alkyl) having a terminal double bond. However, depending on the manner in which the estolide compound is prepared, it is possible that the at least one estolide compound will have internal sites of unsaturation on fatty acid residues that are not the capping group. For example, preparing estolides with a mixture of fatty acid reactants that includes polyunsaturates may result in compounds having internal sites of unsaturation on the base fatty acid residue, or even on one or more of the linking residues. In certain embodiments, subjecting such estolide compounds to cross metathesis conditions will result in estolide base oils having truncated linking and/or base fatty acid residues with at least one terminal site of unsaturation. In certain embodiments, this process provides a method for preparing compounds of Formula V.

In certain embodiments, the at least one estolide compound having at least one fatty acid chain residue with at least one internal site of unsaturation is contacted with at least one alpha olefin in the presence of a metathesis catalyst to provide at least one estolide base oil with at least one fatty acid chain residue having at least one terminal site of unsaturation, and an olefin product. For example, an estolide with an oleate cap may be contacted with an alpha olefin such as ethene (ethylene) in the presence of a metathesis catalyst to provide an estolide base oil with a truncated cap, and a terminal olefin (1-decene), as shown in Scheme 7:

Scheme 7

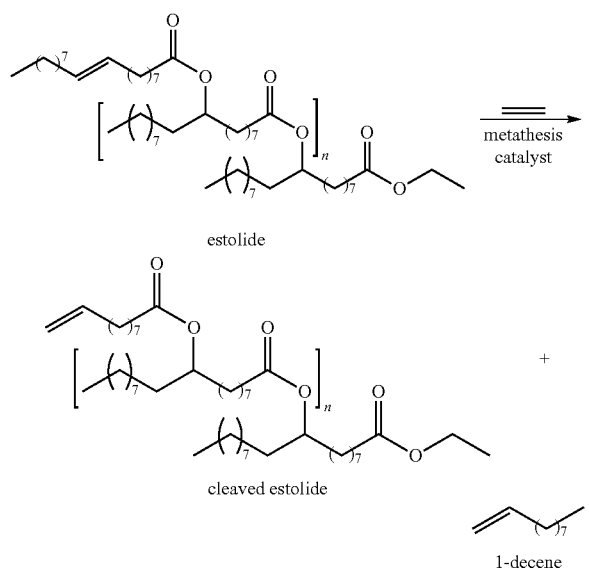

As described above, the at least one estolide compound can be metathesized to provide at least one estolide base oil having at least one fatty acid residue with at least one terminal site of unsaturation. In certain embodiments, the metathesis leaves the at least one estolide compound substantially intact and/or unchanged, but for the cleavage and shortening of the at least one fatty acid residue. For example, as shown above, the metathesis of an estolide comprising an oleic acid cap with ethene will provide an estolide base oil with a $C_{10}$ cap, as well as a cleaved 1-decene terminal olefin. However, in certain embodiments, the cross metathesis of the at least one estolide compound with an alpha olefin having more than 2 carbons, such as 1-butene, provides a mixture of products. For example, the cross metathesis of the at least one estolide compound may provide a mixture of 1-decene and 3-dodecene, and an estolide base oil with individual estolides having a $C_{10}$ cap with a terminal double bond or a $C_{12}$ cap with an internal double bond In certain embodiments, the process of preparing the estolide base oil further comprises functionalizing the terminal site of unsaturation of the at least one fatty acid residue. In certain embodiments, the functionalizing comprises hydrogenating the at least one terminal site of unsaturation. In certain embodiments, the functionalizing comprises reacting the at least one terminal site of unsaturation with at least one carboxylic acid, wherein a covalent bond is formed between an oxygen of a carboxylic group of the at least one carboxylic acid and a carbon of the at least one terminal site of unsaturation. In certain embodiments, the functionalizing comprises halogenating, sulfonating, sulfurizing, or epoxidizing the at least one fatty acid residue. In certain embodiments, the functionalizing comprises the coupling between the terminal site of unsaturation and an aryl or vinyl halide (e.g., Heck reaction). In certain embodiments, the functionalizing comprises the addition of an aldehyde or ketone to the terminal site of unsaturation (e.g., Prins reaction). In certain embodiments, the functionalizing comprises converting the terminal site of unsaturation into a carboxylic acid (e.g., Koch reaction). In certain embodiments, the functionalizing comprises exposing the terminal site of unsaturation to further metathesis conditions in the presence of, for example, and acrylate (e.g., methyl acrylate) to provide a terminal ester. In certain embodiments, the functionalizing comprises reacting the terminal site of unsaturation with water or an alcohol (e.g., under acidic conditions) to form a hydroxyl group or an ether, respectively. In certain embodiments, any of aforementioned functionalizing methods may be accomplished using any of the methods known by persons of ordinary skill in the art.

In another embodiment is described a process of producing compounds comprising:

providing at least one first fatty acid reactant and at least one second fatty acid reactant,
wherein the at least one second fatty acid reactant has at least one terminal site of unsaturation; and
reacting the at least one first fatty acid reactant with the at least one second fatty acid reactant to provide a compound, wherein a covalent bond is formed between an oxygen of a carboxylic group of the at least one first fatty acid reactant and a carbon of the at least one terminal site of unsaturation of the at least one second fatty acid reactant.

In certain embodiments, the at least one first fatty acid reactant is selected from one or more saturated or unsaturated fatty acids. In certain embodiments, the at least one second fatty acid reactant having at least one terminal site of unsaturation is selected from unsaturated fatty acids, unsaturated fatty acid alkyl esters, unsaturated fatty acid glycerides, and unsaturated fatty acid oligomers. In certain embodiments, the at least one second fatty acid reactant having at least one terminal site of unsaturation is prepared by subjecting a fatty acid substrate having at least one internal site of unsaturation to any of the cross metathesis conditions previously described herein, such as those comprising a metathesis catalyst and an alpha olefin (e.g., ethene). In certain embodiments, the fatty acid substrate is selected from one or more unsaturated fatty acid substrates, such as one or more unsaturated fatty acid substrates having at least one internal site of unsaturation selected from one or more triglycerides, one or more diglycerides, one or more monoglycerides, one or more fatty acid alkyl esters, or one or more free fatty acids. In certain embodiments, the at least one second fatty acid reactant is a triglyceride having at least one terminal site of unsaturation, which may be derived from the cross metathesis of a triglyceride substrate having at least one internal site of unsaturation. In certain embodiments, the at least one second fatty acid reactant is a fatty acid having at least one terminal site of unsaturation, which may be derived from the cross metathesis of a fatty acid ester (e.g., triglyceride) substrate having at least one internal site of unsaturation and the subsequent liberation of the truncated fatty acid via glycerine removal. Accordingly, in certain embodiments, the at least one second fatty acid is derived from a process that includes cross metathesis. In certain embodiments, the at least one first and second fatty acid reactants are fatty acids, wherein the first and second fatty acids are derived from a process that includes metathesis.

In certain embodiments, the resulting compound is prepared by reacting the at least one first fatty acid reactant with the at least one second fatty acid reactant having at least one terminal site of unsaturation, wherein a covalent bond is formed between an oxygen of a carboxylic group of the at least one first fatty acid reactant and a carbon of the at least one terminal site of unsaturation of the at least one second fatty acid reactant. In certain embodiments, that at least one first and second fatty acid reactants both comprise at least one terminal site of unsaturation. In certain embodiments, the at least one first fatty acid reactant and at least one second fatty acid reactant comprise the same structure (e.g., $C_{10}$ fatty acid with a terminal double bond prepared from the metathesis of oleic acid with ethene). In certain embodiments, the reacting of the at least one first fatty acid with the at least one second fatty acid takes place in the presence of an oligomerization catalyst, such as those described below. In certain embodiments, the process comprises the oligomerization of one or more free fatty acids.

In certain embodiments, the process of reacting the at least one first fatty acid reactant with the at least one second fatty acid reactant having at least one terminal site of unsaturation provides compounds having a high degree of oligomerization and/or polymerization. For example, in certain embodiments, it is believed that this high degree of oligomerization and/or polymerization is possible because each fatty acid reactant links to the hydrocarbyl terminus of another fatty acid, i.e., at the terminal or penultimate carbon of the fatty acid. Thus, unlike the oligomerization of fatty acids having internal sites of unsaturation, the resulting fatty acid oligomer of unbranched or lightly-branched fatty acids having terminal sites of unsaturation will provide a steric profile that may be more favorable for further oligomerization and increased growth of the molecule. In certain embodiments, this process provides a method for preparing compounds of Formula III.

In certain embodiments, the oligomerization catalyst comprises one or more compounds selected from Bronsted acid catalysts and Lewis acid catalysts. In certain embodiments, the Lewis acid catalyst is selected from one or more triflates (trifluormethanesulfonates) such as transition metal triflates and lanthanide triflates. Suitable triflates may include, but are not limited to, AgOTf (silver triflate), $Cu(OTf)_2$ (copper triflate), NaOTf (sodium triflate), $Fe(OTf)_2$ (iron (II) triflate), $Fe(OTf)_3$ (iron (III) triflate), LiOTf (lithium triflate), $Yb(OTf)_3$ (ytterbium triflate), $Y(OTf)_3$ (yttrium triflate), $Zn(OTf)_2$ (zinc triflate), $Ni(OTf)_2$ (nickel triflate), $Bi(OTf)_3$ (bismuth triflate), $La(OTf)_3$ (lanthanum triflate), and $Sc(OTf)_3$ (scandium triflate). In certain embodiments, the Lewis acid catalyst is $Fe(OTf)_3$. In certain embodiments, the Lewis acid catalyst is $Bi(OTf)_3$. In certain embodiments, the Lewis acid catalyst is $Fe(OTf)_2$.

In certain embodiments, Lewis acid catalyst comprises one or compounds selected from metal compounds, such as iron compounds, cobalt compounds, and nickel compounds. In certain embodiments, the metal compound is selected from one or more of $FeX_n$ (n=2, 3), $Fe(CO)_5$, $Fe_3(CO)_{12}$, $Fe(CO)_3(ET)$, $Fe(CO)_3(DE)$, $Fe(DE)_2$, $CpFeX(CO)_2$, $[CpFe(CO)_2]_2$, $[Cp*Fe(CO)_2]_2$, $Fe(acac)_3$, $Fe(OAc)$. (n=2, 3), $CoX_2$, $Co_2(CO)_8$, $Co(acac)_n$, (n=2, 3), $Co(OAc)_2$, $CpCO(CO)_2$, $Cp*Co(CO)_2$, $NiX_2$, $Ni(CO)_4$, $Ni(DE)_2$, $Ni(acac)_2$, and $Ni(OAc)_2$, wherein X is selected from hydrogen, halogen, hydroxyl, cyano, alkoxy, carboxylato, and thiocyanato; wherein Cp is a cyclopentadienyl group; acac is an acetylacetonato group; DE is selected from norbornadienyl, 1,5-cyclooctadienyl, and 1,5-hexadienyl; ET is selected from ethylenyl and cyclooctenyl; and OAc represents an acetate group. In some embodiments, the Lewis acid is an iron compound. In some embodiments, the Lewis acid is an iron compound selected from one or more of $Fe(acac)_3$, $FeCl_3$, $Fe_2(SO_4)_3$, $Fe_2O_3$, and $FeSO_4$.

In addition, or in the alternative, the oligomerization comprises the use of one or more Bronsted acid catalysts. Exemplary Bronsted acids include, but are not limited to, hydrochloric acid, nitric acid, sulfamic acid, methylsulfamic acid, sulfuric acid, phosphoric acid, perchloric acid, triflic acid, p-toluenesulfonic acid (p-TsOH), and combinations thereof. In certain embodiments, the Bronsted acid is selected from one or more of sulfamic acid and methylsulfamic acid. In some embodiments, the Bronsted acid may comprise cation exchange resins, acid exchange resins and/or solid-supported acids. Such materials may include styrene-divinylbenzene copolymer-based strong cation exchange resins such as Amberlyst® (Rohm & Haas; Philadelphia, Pa.), Dowex® (Dow; Midland, Mich.), CG resins from Resintech, Inc. (West Berlin, N.J.), and Lewatit resins such as MonoPlus™ S 100H from Sybron Chemicals Inc. (Birmingham, N.J.). Exemplary solid acid catalysts include cation exchange resins, such as Amberlyst® 15, Amberlyst® 35, Amberlite® 120, Dowex® Monosphere M-31, Dowex® Monosphere DR-2030, and acidic and acid-activated mesoporous materials and natural clays such a kaolinites, bentonites, attapulgites, montmorillonites, and zeolites. Exemplary catalysts also include organic acids supported on mesoporous materials derived from polysaccharides and activated carbon, such as Starbon®-supported sulphonic acid catalysts (University of York) like Starbon® 300, Starbon® 400, and Starbon® 800. Phosphoric acids on solid supports may also be suitable, such as phosphoric acid supported on silica (e.g., SPA-2 catalysts sold by Sigma-Aldrich).

In certain embodiments, one or more fluorinated sulfonic acid polymers may be used as solid-acid catalysts for the processes described herein. These acids are partially or totally fluorinated hydrocarbon polymers containing pendant sulfonic acid groups, which may be partially or totally converted to the salt form. Exemplary sulfonic acid polymers include Nafion® perfluorinated sulfonic acid polymers such as Nafion® SAC-13 (E.I. du Pont de Nemours and Company, Wilmington, Del.). In certain embodiments, the catalyst comprises a Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton ($H^+$), or the metal salt form. In some embodiments, the oligomerization process comprises use of one or more of protic or aprotic catalysts.

In some embodiments, the oligomerization processes are aided by the application of electromagnetic energy. In certain embodiments, the electromagnetic energy used to aid the oligomerization is microwave electromagnetic energy. In certain embodiments, for example, application of electromagnetic radiation may be applied to reduce the overall reaction time and improve the yield of the compound by conducting the reaction in a microwave reactor in the presence of an oligomerization catalyst. In some embodiments, oligomerizing the at least one first fatty acid reactant with the at least one second fatty acid reactant is conducted in the presence of an oligomerization catalyst (e.g., a Lewis acid) and microwave radiation. In some embodiments, the oligomerization is conducted in a microwave reactor with $Bi(OTf)_3$. In some embodiments, the oligomerization is conducted in a microwave reactor with $Fe(OTf)_3$. In some embodiments, the oligomerization is conducted in a microwave reactor with $Fe(OTf)_2$.

In some embodiments, depending on the nature of the catalyst and the reaction conditions, it may be desirable to carry out the process at a certain temperature and/or pressure. In some embodiments, for example, suitable temperatures for effecting oligomerization may include temperatures greater than about 50° C., such as a range of about 50° C. to about 100° C. In some embodiments, the oligomerization is carried out at about 60° C. to about 80° C. In some embodiments, the oligomerization is carried out, for at least a portion of the time, at about 50° C., about 52° C., about 54° C., about 56° C., about 58° C., about 60° C., about 62° C., about 64° C., about 66° C., about 68° C., about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., and about 100° C. In some embodiments, the oligomerization is carried out, for at least a period of time, at a temperature of no greater than about 52° C., about 54° C., about 56° C., about 58° C., about 60° C., about 62° C., about 64° C., about 66° C., about 68° C., about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., or about 100° C.

In some embodiments, suitable oligomerization conditions may include reactions that are carried out at a pressure of less than 1 atm abs (absolute), such at less than about 250 torr abs, less than about 100 torr abs, less than about 50 torr abs, or less than about 25 torr abs. In some embodiments, oligomerization is carried out at a pressure of about 1 torr abs to about 20 torr abs, or about 5 torr abs to about 15 torr abs. In some embodiments, oligomerization, for at least a period of time, is carried out at a pressure of greater than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, and about 250 torrs abs. In some embodiments, oligomerization, for at least a period of time, is carried out at a pressure of less than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, or about 250 torrs abs.

In certain embodiments, it may be desirable to esterify a free fatty acid compound in the presence of at least one alcohol. Accordingly, in certain embodiments, the processes described herein further comprise the step of esterifying the resulting free acid estolide in the presence of at least one esterification catalyst. Suitable esterification catalysts may include one or more Lewis acids and/or Bronsted acids selected from, for example, AgOTf, $Cu(OTf)_2$, $Fe(OTf)_2$, $Fe(OTf)_3$, NaOTf, LiOTf, $Yb(OTf)_3$, $Y(OTf)_3$, $Zn(OTf)_2$, $Ni(OTf)_2$, $Bi(OTf)_3$, $La(OTf)_3$, $Sc(OTf)_3$, hydrochloric acid, nitric acid, sulfuric acid, phosphoric acid, perchloric acid, triflic acid, p-TsOH, and combinations thereof. In certain embodiments, the esterification catalyst is selected from cation exchange resins, acid exchange resins and/or solid-supported acids, such as those previously described herein. In some embodiments, the esterification catalyst may comprise a strong Lewis acid such as $BF_3$ etherate. In some embodiments, the Lewis acid of the oligomerizing step and the esterification catalyst will be the same, such as $Bi(OTf)_3$. In some embodiments, the esterification is conducted in the presence of microwave radiation.

In some embodiments, the esterification catalyst may comprise a Lewis acid catalyst, for example, at least one metal compound selected from titanium compounds, tin compounds, zirconium compounds, hafnium compounds, and combinations thereof. In some embodiments, the Lewis acid esterification catalyst is at least one titanium compound selected from $TiCl_4$ and $Ti(OCH_2CH_2CH_2CH_3)_4$ (titanium (IV) butoxide). In some embodiments, the Lewis acid esterification catalyst is at least one tin compound selected from $Sn(O_2CCO_2)$ (tin (II) oxalate), SnO, and $SnCl_2$. In some embodiments, the Lewis acid esterification catalyst is at least one zirconium compound selected from $ZrCl_4$, $ZrOCl_2$, $ZrO(NO_3)_2$, $ZrO(SO_4)$, and $ZrO(CH_3COO)_2$. In some embodiments, the Lewis acid esterification catalyst is at least one hafnium compound selected from $HfCl_2$ and $HfOCl_2$. Unless stated otherwise, all metal compounds and catalysts discussed herein should be understood to include their hydrate and solvate forms. For example, in some embodiments, the Lewis acid esterification catalyst may be selected from $ZrOCl_2 \cdot 8H_2O$ and $ZrOCl_2 \cdot 2THF$, or $HfOCl_2 \cdot 2THF$ and $HfOCl_2 \cdot 8H_2O$.

The present disclosure further relates to methods of making compounds according to Formula I, II, III, and V. By way of example, the reaction of an unsaturated fatty acid with an organic acid and the esterification of the resulting free acid estolide are illustrated and discussed in the following Schemes 8 and 9. The particular structural formulas used to illustrate the reactions correspond to those for synthesis of compounds according to Formula V, prior to metathesis of the Formula V precursor; however, the methods apply equally to the synthesis of compounds according to Formula I, II, and III, with use of compounds having structures corresponding to $R_3$ and $R_4$ with a reactive terminal site of unsaturation.

As illustrated below, compound 100 represents an unsaturated fatty acid that may serve as the basis for preparing the estolide compounds described herein.

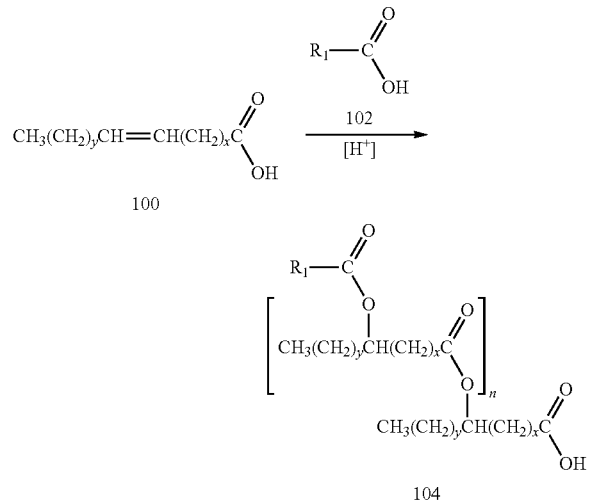

Scheme 8

In Scheme 8, wherein x is, independently for each occurrence, an integer selected from 0 to 20, y is, independently for each occurrence, an integer selected from 0 to 20, n is an integer greater than or equal to 1, and $R_1$ is an optionally substituted alkyl that is saturated or unsaturated, and branched or unbranched, unsaturated fatty acid 100 may be combined with compound 102 and a proton from a proton source to form free acid estolide 104. In certain embodiments, compound 102 is not included, and unsaturated fatty acid 100 may be exposed alone to acidic conditions to form free acid estolide 104, wherein $R_1$ would represent an unsaturated alkyl group. In certain embodiments, if compound 102 is included in the reaction, $R_1$ may represent one or more optionally substituted alkyl residues that are saturated or unsaturated and branched or unbranched. Any suitable proton source may be implemented to catalyze the formation of free acid estolide 104, including but not limited to homogenous acids and/or strong acids like hydrochloric acid, sulfuric acid, perchloric acid, nitric acid, triflic acid, and the like.

Scheme 9

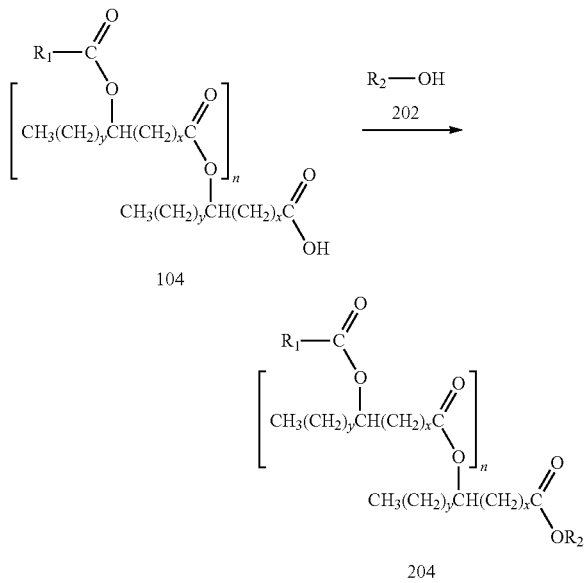

Similarly, in Scheme 9, wherein x is, independently for each occurrence, an integer selected from 0 to 20, y is, independently for each occurrence, an integer selected from 0 to 20, n is an integer greater than or equal to 1, and $R_1$ and $R_2$ are each an optionally substituted alkyl that is saturated or unsaturated, and branched or unbranched, free acid estolide 104 may be esterified by any suitable procedure known to those of skilled in the art, such as acid-catalyzed reduction with alcohol 202, to yield esterified estolide 204. Other exemplary methods may include other types of Fischer esterification, such as those using Lewis acid catalysts such as $BF_3$.

As discussed above, in certain embodiments, the compounds described herein may have improved properties which render them useful as base stocks for biodegradable lubricant applications. Such applications may include, without limitation, crankcase oils, gearbox oils, hydraulic fluids, drilling fluids, two-cycle engine oils, greases, and the like. Other suitable uses may include marine applications, where biodegradability and toxicity are of concern. In certain embodiments, the nontoxic nature of certain estolides described herein may also make them suitable for use as lubricants in the cosmetic and food industries.

In certain embodiments, the estolide compounds may meet or exceed one or more of the specifications for certain end-use applications, without the need for conventional additives. For example, in certain instances, high-viscosity lubricants, such as those exhibiting a kinematic viscosity of greater than about 120 cSt at 40° C., or even greater than about 200 cSt at 40° C., may be desired for particular applications such as gearbox or wind turbine lubricants. Prior-known lubricants with such properties typically also demonstrate an increase in pour point as viscosity increases, such that prior lubricants may not be suitable for such applications in colder environments. However, in certain embodiments, the counterintuitive properties of certain compounds described herein (e.g., increased EN provides estolides with higher viscosities while retaining, or even decreasing, the oil's pour point) may make higher-viscosity estolides particularly suitable for such specialized applications.

Similarly, the use of prior-known lubricants in colder environments may generally result in an unwanted increase in a lubricant's viscosity. Thus, depending on the application, it may be desirable to use lower-viscosity oils at lower temperatures. In certain circumstances, low-viscosity oils may include those exhibiting a viscosity of lower than about 50 cSt at 40° C., or even about 40 cSt at 40° C. Accordingly, in certain embodiments, the low-viscosity estolides described herein may provide end users with a suitable alternative to high-viscosity lubricants for operation at lower temperatures.

In some embodiments, it may be desirable to prepare lubricant compositions comprising an estolide base stock. For example, in certain embodiments, the compounds described herein may be blended with one or more additives selected from polyalphaolefins, synthetic esters, polyalkylene glycols, mineral oils (Groups I, II, and III), pour point depressants, viscosity modifiers, anti-corrosives, antiwear agents, detergents, dispersants, colorants, antifoaming agents, and demulsifiers. In addition, or in the alternative, in certain embodiments, the estolides described herein may be co-blended with one or more synthetic or petroleum-based oils to achieve desired viscosity and/or pour point profiles. In certain embodiments, certain estolides described herein also mix well with gasoline, so that they may be useful as fuel components or additives.

In certain embodiments, the compounds described herein may be considered oligomeric and/or polymeric in nature, and may have use in applications that typically implement polymers. In certain embodiments, the compounds may be useful as lubricants, such as high-viscosity lubricants. In certain embodiments, the compounds may comprise a film or film-like material that may be useful in coating technologies (e.g., inks, paints, film coverings). In certain embodiments, the compounds may comprise a material that is suitable as a plastic additive or plastic alternative. For example, in certain embodiments, the material may be hardened and/or shaped into an article of manufacture, such as housewares (e.g., disposable utensils, storage bins). In certain embodiments, the materials are readily biodegradable and may serve as a substitute for plastics.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance:
NMR spectra were collected using a Bruker Advance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1H$ NMR by a peak at about 4.84 ppm.

Estolide Number (EN):
The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV):

The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I, II, III, and V, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value:

The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC):

GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC:

To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation:

To prepare the samples, 10 mg of estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation:

The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation:

The iodine value is estimated by the following equation based on ASTM Method D97 (ASTM International, Conshohocken, Pa.):

$$IV = \sum 100 \times \frac{A_f \times MW_I \times db}{MV_f}$$

$A_f$=fraction of fatty compound in the sample
$MW_I$=253.81, atomic weight of two iodine atoms added to a double bond
db=number of double bonds on the fatty compound
$MV_f$=molecular weight of the fatty compound The properties of exemplary estolide compounds and compositions described herein are identified in the following examples and tables.

Other Measurements:

Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat #244252) and heated to 60° C. in vacuo (10 torr abs) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (μ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 1). Certain data are reported below in Tables 1 and 6.

Example 2

The acid catalyst reaction was conducted in a 50 gallon Pfaudler RT-Series glass-lined reactor. Oleic acid (50 Kg, OL 700, Twin Rivers) and whole cut coconut fatty acid (18.754 Kg, TRC 110, Twin Rivers) were added to the reactor with 70% perchloric acid (1145 mL, Aldrich Cat #244252) and heated to 60° C. in vacuo (10 torr abs) for 24 hrs while continuously being agitated. After 24 hours the vacuum was released. 2-Ethylhexanol (34.58 Kg) was then added to the reactor and the vacuum was restored. The reaction was allowed to continue under the same conditions (60° C., 10 torr abs) for 4 more hours. At which time, KOH (744.9 g) was dissolved in 90% ethanol/water (5000 mL, 90% EtOH by volume) and added to the reactor to quench the acid. The solution was then allowed to cool for approximately 30 minutes. The contents of the reactor were then pumped through a 1μ filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides (Ex. 2). Certain data are reported below in Tables 2 and 5.

Example 3

The estolides produced in Example 1 (Ex. 1) were subjected to distillation conditions in a Myers 15 Centrifugal Distillation still at 300° C. under an absolute pressure of approximately 12 microns (0.012 torr). This resulted in a primary distillate having a lower EN average (Ex. 3A), and a distillation residue having a higher EN average (Ex. 3B). Certain data are reported below in Tables 1 and 6.

TABLE 1

| Estolide Base Stock | EN | Pour Point (° C.) | Iodine Value (cg/g) |
|---|---|---|---|
| Ex. 3A | 1.35 | −32 | 31.5 |
| Ex. 1 | 2.34 | −40 | 22.4 |
| Ex. 3B | 4.43 | −40 | 13.8 |

Example 4

Estolides produced in Example 2 (Ex. 2) were subjected to distillation conditions in a Myers 15 Centrifugal Distillation still at 300° C. under an absolute pressure of approximately 12 microns (0.012 torr). This resulted in a primary distillate having a lower EN average (Ex. 4A), and a distillation residue having a higher EN average (Ex. 4B). Certain data are reported below in Tables 2 and 7.

TABLE 2

| Estolide Base Stock | EN | Pour Point (° C.) | Iodine Value (cg/g) |
|---|---|---|---|
| Ex. 4A | 1.31 | −30 | 13.8 |
| Ex. 2 | 1.82 | −33 | 13.2 |
| Ex. 4B | 3.22 | −36 | 9.0 |

Example 5

Estolides were made according to the method set forth in Example 1, except that the 2-ethylhexanol esterifying alcohol used in Example 1 was replaced with various other alcohols. Alcohols used for esterification include those identified in Table 3 below. The properties of the resulting estolides are set forth in Table 7.

Table 3, bridging pages 66-67, delete the chemical structure corresponding to "Fineoxocol® 180" at the top of page 67 and replace it with the following chemical structure:

TABLE 3

| Alcohol | Structure |
|---|---|
| Jarcol ™ I-18CG | iso-octadecanol |
| Jarcol ™ I-12 | 2-butyloctanol |
| Jarcol ™ I-20 | 2-octyldodecanol |
| Jarcol ™ I-16 | 2-hexyldecanol |
| Jarcol™ 85BJ | cis-9-octadecen-1-ol |
| Fineoxocol ® 180 | (structure shown) |
| Jarcol™ I-18T | 2-octyldecanol |

Example 6

Estolides were made according to the method set forth in Example 2, except the 2-ethylhexanol esterifying alcohol was replaced with isobutanol. The properties of the resulting estolides are set forth in Table 7.

Example 7

Estolides of Formula I, II, III, and V are prepared according to the method set forth in Examples 1 and 2, except that the 2-ethylhexanol esterifying alcohol is replaced with various other alcohols. Alcohols to be used for esterification include those identified in Table 4 below. Esterifying alcohols to be used, including those listed below, may be saturated or unsaturated, and branched or unbranched, or substituted with one or more alkyl groups selected from methyl, ethyl, propyl, isopropyl, butyl, isobutyl, sec-butyl, tert-butyl, pentyl, isopentyl, neopentyl, hexyl, isohexyl, and the like, to form a branched or unbranched residue at the $R_2$ position. Examples of combinations of esterifying alcohols and $R_2$ Substituents are set forth below in Table 4:

TABLE 4

| Alcohol | $R_2$ Substituents |
|---|---|
| $C_1$ alkanol | methyl |
| $C_2$ alkanol | ethyl |
| $C_3$ alkanol | n-propyl, isopropyl |
| $C_4$ alkanol | n-butyl, isobutyl, sec-butyl |
| $C_5$ alkanol | n-pentyl, isopentyl neopentyl |
| $C_6$ alkanol | n-hexyl, 2-methyl pentyl, 3-methyl pentyl, 2,2-dimethyl butyl, 2,3-dimethyl butyl |
| $C_7$ alkanol | n-heptyl and other structural isomers |
| $C_8$ alkanol | n-octyl and other structural isomers |
| $C_9$ alkanol | n-nonyl and other structural isomers |
| $C_{10}$ alkanol | n-decanyl and other structural isomers |
| $C_{11}$ alkanol | n-undecanyl and other structural isomers |
| $C_{12}$ alkanol | n-dodecanyl and other structural isomers |
| $C_{13}$ alkanol | n-tridecanyl and other structural isomers |
| $C_{14}$ alkanol | n-tetradecanyl and other structural isomers |
| $C_{15}$ alkanol | n-pentadecanyl and other structural isomers |
| $C_{16}$ alkanol | n-hexadecanyl and other structural isomers |
| $C_{17}$ alkanol | n-heptadecanyl and other structural isomers |
| $C_{18}$ alkanol | n-octadecanyl and other structural isomers |
| $C_{19}$ alkanol | n-nonadecanyl and other structural isomers |
| $C_{20}$ alkanol | n-icosanyl and other structural isomers |
| $C_{21}$ alkanol | n-heneicosanyl and other structural isomers |
| $C_{22}$ alkanol | n-docosanyl and other structural isomers |

TABLE 6

| PROPERTY | ADDITIVES | ASTM METHOD | Ex. 3A | Ex. 1 | Ex. 3B |
|---|---|---|---|---|---|
| Color | None | — | Light Gold | Amber | Amber |
| Specific Gravity (15.5° C.), g/ml | None | D 4052 | 0.897 | 0.906 | 0.917 |
| Viscosity - Kinematic at 40° C., cSt | None | D 445 | 40.9 | 91.2 | 211.6 |
| Viscosity - Kinematic at 100° C., cSt | None | D 445 | 8.0 | 14.8 | 27.8 |
| Viscosity Index | None | D 2270 | 172 | 170 | 169 |
| Pour Point, ° C. | None | D 97 | −32 | −40 | −40 |
| Cloud Point, ° C. | None | D 2500 | −32 | −33 | −40 |
| Flash Point, ° C. | None | D 92 | 278 | 286 | 306 |
| Fire Point, ° C. | None | D 92 | 300 | 302 | 316 |
| Evaporative Loss (NOACK), wt. % | None | D 5800 | 1.4 | 0.8 | 0.3 |
| Vapor Pressure - Reid (RVP), psi | None | D 5191 | ≈0 | ≈0 | ≈0 |

TABLE 7

| Example # | Alcohol | Estimated EN (approx.) | Pour Pt. ° C. | Cloud Pt. ° C. | Visc. @ 40° C. | Visc. @ 100° C. | Visc. Index |
|---|---|---|---|---|---|---|---|
| 8 | Jarcol ™ I-18CG | 2.0-2.6 | −15 | −13 | 103.4 | 16.6 | 174 |
| 8 | Jarcol ™ I-12 | 2.0-2.6 | −39 | −40 | 110.9 | 16.9 | 166 |
| 8 | Jarcol ™ I-20 | 2.0-2.6 | −42 | <−42 | 125.2 | 18.5 | 166 |
| 8 | Jarcol ™ I-16 | 2.0-2.6 | −51 | <−51 | 79.7 | 13.2 | 168 |
| 8 | Jarcol ™ 85BJ | 2.0-2.6 | −15 | −6 | 123.8 | 19.5 | 179 |
| 8 | Fineoxocol ® 180 | 2.0-2.6 | −39 | −41 | 174.2 | 21.1 | 143 |
| 8 | Jarcol ™ I-18T | 2.0-2.6 | −42 | <−42 | 130.8 | 19.2 | 167 |
| 8 | Isobutanol | 2.0-2.6 | −36 | −36 | 74.1 | 12.6 | 170 |
| 9 | Isobutanol | 1.5-2.2 | −36 | −36 | 59.5 | 10.6 | 170 |

TABLE 5

| PROPERTY | ADDITIVES | ASTM METHOD | Ex. 4A | Ex. 2 | Ex. 4B |
|---|---|---|---|---|---|
| Color | None | — | Light Gold | Amber | Amber |
| Specific Gravity (15.5° C.), g/ml | None | D 4052 | 0.897 | 0.904. | 0.912 |
| Viscosity - Kinematic at 40° C., cSt | None | D 445 | 32.5 | 65.4 | 137.3 |
| Viscosity - Kinematic at 100° C., cSt | None | D 445 | 6.8 | 11.3 | 19.9 |
| Viscosity Index | None | D 2270 | 175 | 167 | 167 |
| Pour Point, ° C. | None | D 97 | −30 | −33 | −36 |
| Cloud Point, ° C. | None | D 2500 | −30 | −32 | −36 |
| Flash Point, ° C. | None | D 92 | 278 | 264 | 284 |
| Fire Point, ° C. | None | D 92 | 300 | 300 | 320 |
| Evaporative Loss (NOACK), wt. % | None | D 5800 | 1.9 | 1.4 | 0.32 |
| Vapor Pressure - Reid (RVP), psi | None | D 5191 | ≈0 | ≈0 | ≈0 |

Example 8

Saturated and unsaturated estolides having varying acid values were subjected to several corrosion and deposit tests. These tests included the High Temperature Corrosion Bench Test (HTCBT) for several metals, the ASTM D130 corrosion test, and the MHT-4 TEOST (ASTM D7097) test for correlating piston deposits. The estolides tested having higher acid values (0.67 mg KOH/g) were produced using the method set forth in Examples 1 and 4 for producing Ex. 1 and Ex. 4A (Ex. 1* and Ex. 4A* below). The estolides tested having lower acid values (0.08 mg KOH/g) were produced using the method set forth in Examples 1 and 4 for producing Ex. 1 and Ex. 4A except the crude free-acid estolide was worked up and purified prior to esterification with $BF_3.OET_2$ (0.15 equiv.; reacted with estolide and 2-EH in Dean Stark trap at 80° C. in vacuo (10 torr abs) for 12 hrs while continuously being agitated; crude reaction product washed 4×$H_2O$; excess 2-EH removed by heating washed reaction product to 140° C. in vacuo (10 torr abs) for 1 hr) (Ex. 4A # below). Estolides having an IV of 0 were hydrogenated via 10 wt. % palladium embedded on carbon at 75° C. for 3 hours under a pressurized hydrogen atmosphere (200 psig) (Ex. 4A*H and Ex. 4A # H below) The corrosion and deposit tests were performed with a Dexos™ additive package. Results were compared against a mineral oil standard:

TABLE 8

|  | Standard | Ex. 1* Estolide | Ex. 4A* Estolide | Ex. 4A*H Estolide | Ex. 4A# Estolide | Ex. 4A#H Estolide |
|---|---|---|---|---|---|---|
| Acid Value (mg KOH/g) | — | ~0.7 | 0.67 | 0.67 | 0.08 | 0.08 |
| Iodine Value (IV) | — | ~45 | 16 | 0 | 16 | 0 |
| HTCBT Cu | 13 | 739 | 279 | 60 | 9.3 | 13.6 |
| HTCBT Pd | 177 | 11,639 | 1,115 | 804 | 493 | 243 |
| HTCBT Sn | 0 | 0 | 0 | 0 | 0 | 0 |
| ASTM D130 | 1A | 4B | 3A | 1B | 1A | 1A |
| MHT-4 | 18 | 61 | 70 | 48 | 12 | 9.3 |

Example 9

"Ready" and "ultimate" biodegradability of the estolide produced in Ex. 1 was tested according to standard OECD procedures. Results of the OECD biodegradability studies are set forth below in Table 9:

TABLE 9

|  | 301D 28-Day (% degraded) | 302D Assay (% degraded) |
|---|---|---|
| Canola Oil | 86.9 | 78.9 |
| Ex. 1 Base Stock | 64.0 | 70.9 |

Example 10

The Ex. 1 estolide base stock from Example 1 was tested under OECD 203 for Acute Aquatic Toxicity. The tests showed that the estolides are nontoxic, as no deaths were reported for concentration ranges of 5,000 mg/L and 50,000 mg/L.

Example 11

Estolides prepared according to the method set forth in Example 1 (20 mol) and a second-generation Grubbs' catalyst (e.g., C827, 25 ppm) are added to a Parr Reactor and degassed with argon for 1 hr. 1-Butene is added while heating to 60° C. while keeping the pressure of the reaction between about 25 to about 60 psi. The 1-butene is added using a one-way check valve to prevent backflow into the 1-butene cylinder. After 4 hrs, the pressure is released and vented into the fume hood. After allowing the reactor to cool to room temperature, a 50 ml 1M tris-hydroxymethylphopshine (THMP) solution in isopropanol (IPA) (50 mol equiv.) is added, and the reactor is degassed with argon and heated to 60° C. for 18 hrs. The reactor is then again allowed to cool to room temperature. The crude reaction product is then washed with water and brine. The washed reaction product is them dried over sodium sulfate, filtered, and distilled to provide 1-decene, 3-dodecene, estolides having a $C_{10}$ cap with a terminal double bond, and estolides having a $C_{12}$ cap with an internal double bond.

Example 12

Methyl oleate (20 mol) and a second-generation Grubbs' catalyst (e.g., C827, 25 ppm) are added to a Parr Reactor and degassed with argon for 1 hr. 1-Butene is added while heating to 60° C. while keeping the pressure of the reaction between about 25 to about 60 psi. The 1-butene is added using a one-way check valve to prevent backflow into the 1-butene cylinder. After 4 hrs, the pressure is released and vented into the fume hood. After allowing the reactor to cool to room temperature, a 50 ml 1M tris-hydroxymethylphosphine (THMP) solution in isopropanol (IPA) (50 mol equiv.) is added, and the reactor is degassed with argon and heated to 60° C. for 18 hrs. The reactor is then again allowed to cool to room temperature. The crude reaction product is then washed with water and brine. The washed reaction product is them dried over sodium sulfate, filtered, and distilled to provide 1-decene, 3-dodecene, 9-decenoic acid methyl ester, and 9-dodecenoic acid methyl ester.

The 9-dodecenoic acid methyl ester is then hydrolyzed under basic conditions (reflux with an excess of dilute aqueous NaOH), followed by removal of methanol. The resulting aqueous solution is then treated with an excess of dilute HCl, and the solution is distilled to provide 9-dodecenoic acid. Estolides are then prepared according to the methods set forth in Examples 1 and 2, wherein the oleic acid is replaced with 9-dodecenoic acid.

Example 13

9-decenoic acid methyl ester prepared according to the method set forth in Example 12 is isolated then hydrolyzed under basic conditions (reflux with an excess of dilute aqueous NaOH), followed by removal of methanol. The resulting aqueous solution is then treated with an excess of dilute HCl, and the solution is distilled to provide 9-decenoic acid. Oligomers are then prepared according to the methods set forth in Examples 1 and 2, wherein the oleic acid is replaced with 9-decenoic acid.

Example 14

Compounds are prepared according to the methods set forth in Example 12, except methyl oleate is replaced with high-oleic soybean oil (Vistive® Gold, Monsanto Co.) to give a metathesized triglyceride intermediate, which is subsequently hydrolyzed to provide 9-decenoic acid and 9-dodecenoic acid. Estolides are then prepared according to the methods set forth in Examples 1 and 2, wherein oleic acid is replaced with 9-decenoic acid and 9-dodecenoic acid.

Example 15

Compounds are prepared according to the methods set forth in Examples 12 and 14, except 1-butene is replaced with ethene to provide 1-decene and 9-decenoic acid esters as products. The esters are hydrolyzed, and estolides are prepared according to the methods set forth in Examples 1 and 2, wherein oleic acid is replaced with 9-decenoic acid.

Example 16

Compounds are prepared according to the methods set forth in Examples 12-15. The resulting products are then hydrogenated via 10 wt. % palladium embedded on carbon at 75° C. for 3 hours under a pressurized hydrogen atmosphere (200 psig) to provide saturated oligomeric compounds.

The invention claimed is:

1. A process of producing an estolide base oil comprising:
   providing at least one triglyceride having at least one oleic acid residue;
   providing at least one alpha olefin selected from one or more of ethene, propene, 1-butene, 1-pentene, 1-hexene, 1-heptene, or 1-octene;
   contacting the at least one triglyceride with the at least one alpha olefin in the presence of a metathesis catalyst to provide an olefin product comprising 1-decene, and a metathesized fatty acid product comprising at least one 9-decenoic acid residue;
   hydrolyzing the metathesized fatty acid product to provide a free fatty acid product comprising 9-decenoic acid;
   providing an oligomerization catalyst; and
   oligomerizing the 9-decenoic acid with a second fatty acid in the presence of the oligomerization catalyst to produce an estolide base oil, wherein said oligomerizing comprises forming a covalent bond between an oxygen of a carboxylic group of the second fatty acid and a carbon of the double bond of the 9-decenoic acid.

2. The process according to claim 1, wherein the oligomerization catalyst is selected from a Bronsted acid and a Lewis acid.

3. The process according to claim 1, wherein the oligomerization catalyst is a Bronsted acid.

4. The process according to claim 1, wherein the metathesis catalyst is an osmium or ruthenium alkylidene metathesis catalyst.

5. The process according to claim 1, further comprising esterifying the resulting estolide base oil with at least one alcohol to provide an esterified estolide base oil.

6. At least one compound according to Formula III:

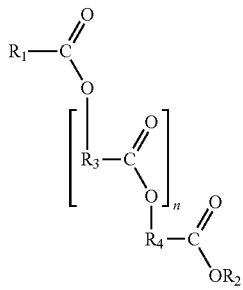

Formula III wherein
n is an integer selected from 0 to 20;
$R_1$ is an unsubstituted, branched or unbranched $C_7$ to $C_{17}$ alkyl that is saturated or unsaturated;
$R_2$ is an unsubstituted $C_1$ to $C_{22}$ alkyl that is saturated or unsaturated, and branched or unbranched; and
$R_3$ and $R_4$, independently for each occurrence, are selected from

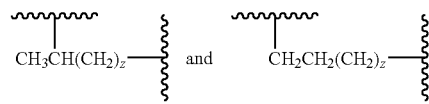

wherein $R_3$ and $R_4$ are unsubstituted and z is 7.

7. The process according to claim 1, wherein the at least one alpha olefin is 1-butene.

8. The process according to claim 7, wherein the olefin product further comprises 3-dodecene.

9. The process according to claim 7, wherein the free fatty acid product further comprises 9-dodecenoic acid.

10. The process according to claim 1, wherein the at least one alpha olefin is ethene.

11. The process according to claim 10, wherein the olefin product consists essentially of 1-decene.

12. The process according to claim 10, wherein the free fatty acid product consists essentially of 9-decenoic acid.

13. The process according to claim 1, wherein the second fatty acid is a saturated fatty acid or an unsaturated fatty acid.

14. The process according to claim 13, wherein the second fatty acid is 9-decenoic acid.

15. The at least one compound according to claim 6, wherein $R_1$ is selected from the structure of Formula IV:

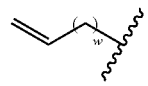

Formula IV wherein w is an integer selected from 5 to 7.

16. The at least one compound according to claim 6, wherein $R_1$ is saturated and unbranched.

17. The at least one compound according to claim 6, wherein $R_2$ is an unsubstituted, branched or unbranched $C_1$ to $C_{18}$ alkyl that is saturated or unsaturated.

18. The at least one compound according to claim 17, wherein $R_2$ is branched and saturated.

19. The at least one compound according to claim 6, wherein n is an integer selected from 0 to 12.

* * * * *